United States Patent [19]

Hansen et al.

[11] Patent Number: 5,589,471

[45] Date of Patent: Dec. 31, 1996

[54] VITAMIN D ANALOGUES CONTAINING A HYDROXY OR ALKYLATED HYDROXY GROUP IN THE 20-POSITION

[75] Inventors: Kai Hansen, Herley; Claus Aage S. Bretting, Frederiksberg, both of Denmark

[73] Assignee: Fabrik Produktionsaktieselskab Leo Pharmaceutical Products Ltd., Ballerup, Denmark

[21] Appl. No.: 362,550

[22] PCT Filed: Sep. 27, 1993

[86] PCT No.: PCT/DK93/00311

§ 371 Date: Jan. 3, 1995

§ 102(e) Date: Jan. 3, 1995

[87] PCT Pub. No.: WO94/07842

PCT Pub. Date: Apr. 14, 1994

[30] Foreign Application Priority Data

Sep. 28, 1992 [GB] United Kingdom .................. 9220439

[51] Int. Cl.[6] ......................... A61K 31/59; C07C 401/00
[52] U.S. Cl. ............................................. 514/167; 552/653
[58] Field of Search ............................. 552/653; 514/167

[56] References Cited

U.S. PATENT DOCUMENTS 5,403,940  4/1995  Vallós et al. ............................. 549/300

FOREIGN PATENT DOCUMENTS 909991  9/1990  WIPO .

OTHER PUBLICATIONS

Kubodera, et al.; "Synthetic Studies of Vitamin D Analogues, XI. Synthesis and Differentiation–Inducing Activity of 1alpha,25-Dihydroxy-22-oxavitamin D3 Analogues", Chemical Parmaceutical Bull., vol. 40, No. 6, Jun. 1, 1992–pp. 1494–1499.

Brown, et al.: "New Active analogues of vitamin D with low calcemic activity", Kidney International, vol. 38, No. 29, 1990, pp. S–22–S–27.

Primary Examiner—Kimberly J. Prior
Attorney, Agent, or Firm—Cushman Darby & Cushman, LLP

[57] ABSTRACT

Compounds of formula

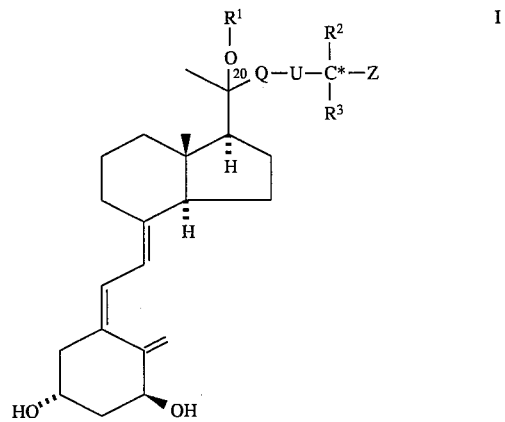

wherein Q is a —$CH_2$—, —CH=CH— or —C≡C—; U is a $C_1$–$C_6$ alkylene; $R^1$ is hydrogen, a $C_1$–$C_4$ alkyl or YR' in which Y stands for the radicals —SO— or —$SO_2$— and R' stands for a $C_1$–$C_4$ alkyl; $R^2$ and $R^3$ are independently hydrogen or $C_1$–$C_4$ alkyl, and additionally $R^2$ and $R^3$, when taken together with the starred carbon atom, may form a $C_3$–$C_6$ carbocyclic ring; Z is hydrogen or hydroxy; and derivatives thereof. The compounds show antiinflammatory and immunomodulating effects as well as strong activity in inducing differentiation and inhibiting undesirable proliferation of certain cells. The compounds are prepared by adding an anion R[−] to 1(S),1(R)-bis-(tert-butyldimethylsilyl-oxy)-9,10-secopregna-5(E),7(E),10(19)-triene-20-one and the resulting compound is alkylated or acylated with $R^1X^1$ where $X^1$ is a leaving group followed by triplet-sensitized photoisomerization and deprotection to give the compound of formula I.

9 Claims, No Drawings

VITAMIN D ANALOGUES CONTAINING A HYDROXY OR ALKYLATED HYDROXY GROUP IN THE 20-POSITION

This invention relates to a hitherto unknown class of compounds which shows antiinflammatory and immunomodulating effects as well as strong activity in inducing differentiation and inhibiting undesirable proliferation of certain cells, including cancer cells and skin cells, to pharmaceutical preparations containing these compounds, to dosage units of such preparations, and to their use in the treatment and prophylaxis of hyperparathyroidism, particularly secondary hyperparathyroidism associated with renal failure, of a number of disease states including diabetes mellitus, hypertension, acne, alopecia, skin ageing, imbalance in the immune system, of inflammatory diseases such as rheumatoid arthritis and asthma, of diseases characterized by abnormal cell differentiation and/or cell proliferation such as e.g. psoriasis and cancer, for prevention and/or treatment of steroid induced skin atrophy, and for promoting osteogenesis and treating osteoporosis.

The compounds of the present invention are represented by the general formula I

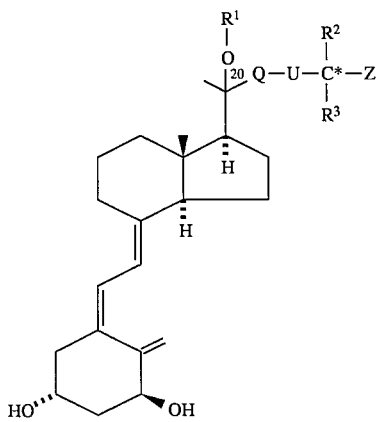

in which formula Q is a —$CH_2$—, —CH=CH— or —C≡C—; U is a $C_1$–$C_6$ alkylene, $R^1$ is hydrogen, a $C_1$–$C_4$ alkyl or YR' in which Y stands for the radicals —SO— or —$SO_2$— and R' stands for a $C_1$–$C_4$ alkyl.

$R^2$ and $R^3$ are independently hydrogen or $C_1$–$C_4$ alkyl, additionally $R^2$ and $R^3$, when taken together with the starred carbon atom, may form a $C_3$–$C_6$ carbocyclic ring; Z is hydrogen or hydroxy.

$R^2$, $R^3$, and U may optionally and independently be substituted with one or more fluorine atoms.

Examples of $R^2$ and $R^3$ when taken separately include, but are not limited to hydrogen, methyl, ethyl, normal and isopropyl.

Examples of $R^2$ and $R^3$ when taken together include ethylene, tri-, tetra-, and pentamethylene.

Examples of U include methylene, ethylene, tri-, tetra-, and pentamethylene.

Particularly preferred compounds include such in which Q is —$CH_2$—, U is —$(CH_2)_2$—, $R^1$ is hydrogen, methyl or ethyl, $R^2$ and $R^3$ are ethyl and Z is hydroxy.

As can be seen from formula I, the compounds of the invention comprise several diastereoisomeric forms (e.g. R or S configuration at C-20 or at the starred carbon atom, E or Z configuration of a side chain double bond). The invention covers all these diastereoisomers in pure form as well as mixtures of such diastereoisomers.

Particularly preferred compounds are compounds containing a saturated side chain with the S-configuration at C-20.

In addition, prodrugs of I in which one or more of the hydroxy groups are masked as groups which can be reconverted to hydroxy groups in vivo are also within the scope of the invention.

The compounds I in which Z is hydrogen are actually another type of prodrug. These compounds are relatively inactive in vitro, but are converted to active compounds of formula I by enzymatic side chain hydroxylation after administration to the patient.

It has been shown that 1α,25-dihydroxy-vitamin $D_3$ (1,25$(OH)_2D_3$) influences the effects and/or production of interleukins (Muller, K. et al, Immunol. Lett. 17, 361–366 (1988)), indicating the potential use of this compound in the treatment of diseases characterized by a dysfunction of the immune system, e.g. autoimmune diseases, AIDS, host versus graft reactions, and rejection of transplants or other conditions characterized by an abnormal interleukin-1 production, e.g. inflammatory diseases such as rheumatoid arthritis and asthma.

It has also been shown that 1,25$(OH)_2D_3$ is able to stimulate the differentiation of cells and inhibit excessive cell proliferation (Abe, E. et al, Proc. Natl. Acad. Sci., U.S.A. 78, 4990–4994 (1981)), and it has been suggested that this compound might be useful in the treatment of diseases characterized by abnormal cell proliferation and/or cell differentiation such as leukemia, myelofibrosis and psoriasis.

Also, the use of 1,25$(OH)_2D_3$, or its pro-drug 1α-OH-$D_3$, for the treatment of hypertension (Lind, L. et al, Acta Med. Scand. 222, 423–427 (1987)) and diabetes mellitus (Inomata, S. et al, Bone Mineral 1, 187–192 (1986)) has been suggested. Another indication for 1,25$(OH)_2D_3$ is suggested by the recent observation of an association between hereditary vitamin D resistance and alopecia: treatment with 1,25$(OH)_2D_3$ may promote hair growth (Editorial, Lancet, Mar. 4, 1989, p. 478). Also, the fact that topical application of 1,25$(OH)_2D_3$ reduces the size of sebaceous glands in the ears of male Syrian hamsters suggests that this compound might be useful for the treatment of acne (Malloy, V. L. et al., the Tricontinental Meeting for Investigative Dermatology, Washington, 1989).

However, the therapeutic possibilities in such indications of 1,25$(OH)_2D_3$ are severely limited by the well known potent effect of this hormone on calcium metabolism; elevated blood concentrations will rapidly give rise to hypercalcemia. Thus, this compound and its potent synthetic analogues are not completely satisfactory for use as drugs in the treatment of e.g. psoriasis, leukemia or immune diseases which may require continuous administration of the drug in relatively high doses.

A number of vitamin D analogues have recently been described which show some degree of selectivity in favour of the cell differentiation inducing/cell proliferation inhibiting activity as compared with the effect on calcium metabolism.

Thus, the vitamin $D_3$ analogue, calcipotriol, containing a 22,23-double bond, a 24-hydroxy group and in which the carbon atoms 25, 26 and 27 are incorporated in a three membered ring, is a potent inducer of cell differentiation and inhibitor of cell proliferation which shows only moderate activity on calcium metabolism in vivo (Binderup, L. and Bramm, E., Biochem. Pharmacol. 37, 889–895 (1988)).

However, this selectivity is not paralleled by in vitro studies, which show that calcipotriol binds equally well as 1,25$(OH)_2D_3$ to the intestinal vitamin D receptor. Possibly, the low in vivo activity on calcium metabolism of calcipotriol is due to a rapid metabolism of the compound, thus limiting the potential of this compound for systemic use.

24-Homo-1,25-dihydroxyvitamin $D_3$ and 26-homo-1,25-dihydroxyvitamin $D_3$ (together with their 22,23-didehydro-analogues) (Ostrem, V. K.; Tanaka, Y.; Prahl, J.; DeLuca, H. F.; and Ikekawa, N.; Proc. Natl. Acad. Sci. U.S.A. 84, 2610–14 (1987)) have been claimed to have the same binding affinity as $1,25(OH)_2D_3$ to both the rat and chicken intestinal receptor and the receptor in a human myeloid leukemia cell line (HL-60), and yet to be 10-fold more potent than $1,25(OH)_2D_3$ in inducing differentiation of HL-60 cells in vitro. In vivo, these compounds are respectively "significantly less potent" and "more potent" than $1,25(OH)_2D_3$ in calcium metabolism assessments.

26,27-Dimethyl-1,25-dihydroxyvitamin $D_3$ has been synthesized, but the published information regarding its biological activities is contradictory. (Sai, H.; Takatsuto, S.; Hara, N.; and Ikekawa, N.; Chem. Pharm. Bull. 33, 878–881 (1985) and Ikekawa, N.; Eguchi, T.; Hara, N.; Takatsuto, S.; Honda, A.; Mori, Y.; and Otomo, S.; Chem. Pharm. Bull. 35, 4362–4365 (1987)). The closely related 26,27-diethyl-1,25-dihydroxyvitamin $D_3$ is also reported by these authors; in this case as having "almost no vitamin D activity" (i.e. calcium metabolism effects) while being 10-fold more potent than $1,25(OH)_2D_3$ in inducing cell differentiation.

U.S. Pat. No. 4,804,502 discloses compounds containing a triple bond in the side chain of Vitamin D, and these compounds are claimed to be useful in the treatment of disease states characterized by metabolic calcium deficiencies.

The fact that there are only small structural differences between the compounds of the prior art referred to above indicates that the present state of knowledge does not allow prediction of the structure of vitamin D analogues which will show a favourable degree of selectivity, as reflected by a higher cell differentiating activity in vitro compared to the binding affinity for intestinal vitamin D receptor in vitro. Furthermore, the matter is complicated by the observation that receptor binding affinities in vitro are not always paralleled by in vivo studies, probably reflecting a pharmacokinetic difference between the compounds.

Also compounds which differ structurally from the above vitamin D analogues in the configuration of the methyl group at carbon-20 have been reported to have potent effects on cell differentiation/proliferation. This "unnatural" configuration, present in several recent patent applications including our previous international patent application number PCT/DK90/00156, filing date 19th Jun., 1990, publication number WO 91/00271, and international patent application number PCT/DK91/00200, filing date 11th Jul., 1991, publication number WO 92/03414, has surprisingly been found to have a profound and advantageous biological significance.

The hydroxy groups in the side chain of vitamin D or its analogues seems to be essential for biological activity, but the introduction of further hydroxy groups in the side chain normally leads to inactive or less active compounds (Eguchi T.; Yoshida M.; and Ikekawa N.; Bioorg. Chem 17, 294 (1989); Eur. Pat. Appl. EP 296800, 28. Dec. 1988).

The compounds of the present invention differ structurally from the known vitamin D analogues in containing a hydroxy group or an alkylated hydroxy group in the 20-position. The compounds have surprisingly been found to be highly active and to show favourable selectivity. Thus, a compound of formula I is observed to show one or more of the following advantages when comparison to prior art is made:

(a) more potent effects on cell differentiation/proliferation
(b) a greater selectivity in favour of the potent effects on cell differentiation/proliferation contra the effects on calcium metabolism;
(c) more potent effects on the production and action of interleukins;
(d) a greater selectivity in favour of the effects on interleukin production and action versus the effects on calcium metabolism.

The compounds of the invention are therefore especially suited for both local and systemic treatment and prophylaxis of human and veterinary disorders which are characterized by 1) abnormal cell proliferation and/or cell differentiation, such as certain dermatological disorders including psoriasis and certain cancer forms, 2) an imbalance in the immune system, e.g. in autoimmune diseases, including diabetes mellitus, host versus graft reaction, and rejection of transplants; and additionally for the treatment of inflammatory diseases, such as rheumatoid arthritis and asthma. Acne, alopecia, and hypertension are other conditions which may be treated with the compounds of the invention. Finally, as thickening of the skin may be observed after topical treatment with the compounds of the invention, these compounds may be useful for treatment or prevention of skin ageing, including photo-ageing.

Because of the low tendency of the compounds to produce hypercalcemia on continued administration they are expected to be valuable for the long term treatment of hyperparathyroidism (particularly secondary hyperparathyroidism associated with renal failure) and for promoting osteogenesis and treating osteoporosis. For these indications the presently described compounds have a higher therapeutic ratio than the prior art compounds (see U.S. Pat. No. 4,948,789 and EP 0385446 A2).

The present compounds may be used in combination with other pharmaceuticals. In the prevention of graft rejection and graft versus host reaction, a treatment with the present compounds may advantageously be combined with e.g. a cyclosporin treatment.

The compounds of formula I may conveniently be prepared from the vitamin D derivative 1 (Hansen K., Calverley M. J. and Binderup L.: Synthesis and Biological Activity of 22-Oxa Vitamin D analogues. In: Vitamin D, Proc. Eighth Workshop on Vitamin D, Paris, Jul. 5–10, 1991, p. 161; Walther de Gruyter, Berlin 1991) by the routes outlined in Scheme 1.

The following standard abbreviations are used throughout this disclosure: Me=methyl; Et=ethyl; Pr=n-propyl; Bu=n-butyl; THP=tetrahydro-4H-pyran-2-yl; TMS=trimethylsilyl; DMAP=4-dimethylaminopyridine; pet.ether=petroleum ether; THF=tetrahydrofuran; TBAF=tetra-(n-butyl)-ammonium fluoride trihydrate; b.p.=boiling point; PLC=preparative thin-layer chromatography; Tf=trifluoromethane sulphonyl; DMF=N,N-dimethylformamide; "HF"=5% hydrogen fluoride in acetonitrile:water (7:1); TBDMS=tert-butyldiemthylsilyl; HCl=hydrochloric acid; "NaHCO$_3$"= saturated aqueous sodium bicarbonate solution; $A^1A^2A^3SiX^2$: a silylating agent where $A^1$, $A^2$ and $A^3$, which may be the same or different, stand for $C_1$–$C_6$ alkyl, $C_1$–$C_6$ alkyloxy, or aryl, and $X^2$ stands for a good leaving group, such as —Cl, —Br or —OTf (trifluoromethane sulphonate or triflate); PPTS=pyridinium toluene-4-sulphonate.

Scheme 1
Synthesis of the Compounds of Formula I

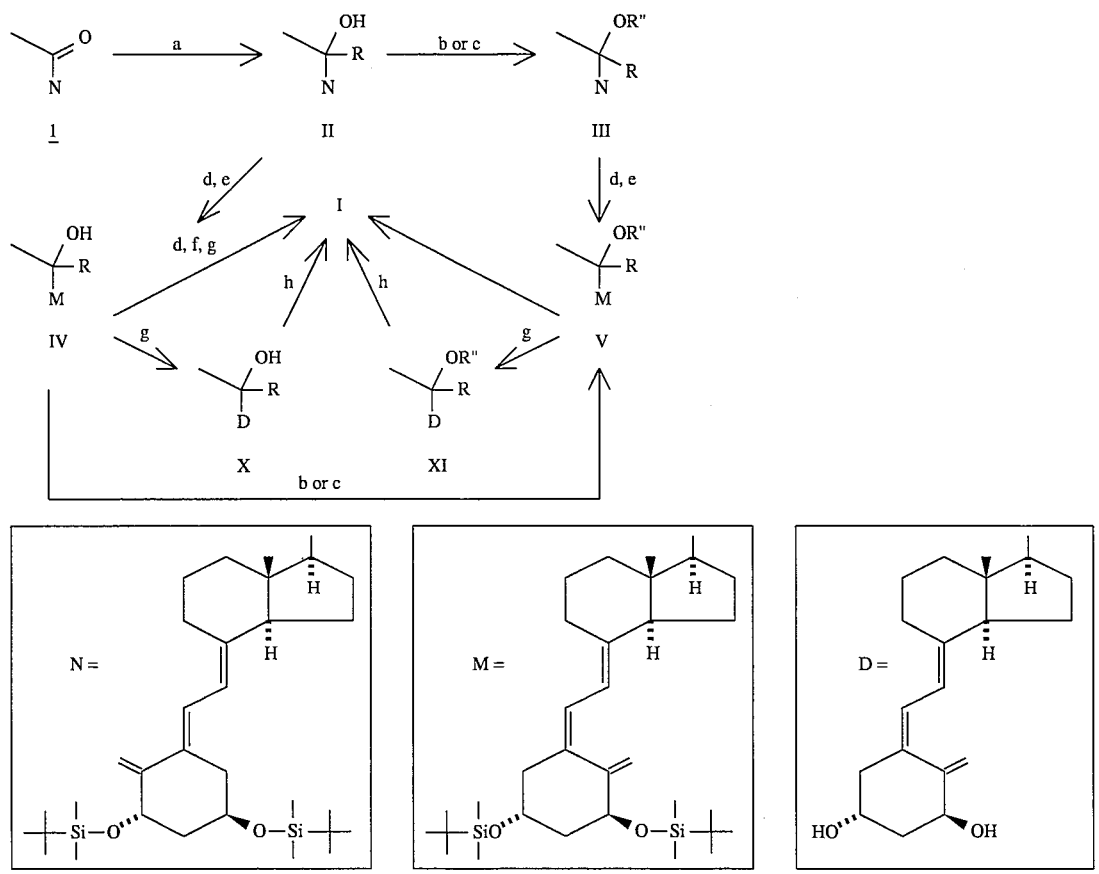

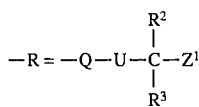

$Z^1$ = H or $OR^4$
$R^4$ = hydrogen or an alcohol protective group (e.g. trialkylsilyl or THP)
R" = $C_1$–$C_{10}$ alkyl or YR'
Q, U, $R^2$, $R^3$, Y and R' are as defined above Notes to Scheme 1 a  Addition of the anion R⁻, such as in RLi, or the Grignard reagent $RMgX^1$ ($X^1$ = a halogen, such as Cl, Br or I), derived from the side chain building block $RX^1$, to tthe carbonyl group of compound 1.
b  Alkylation of the C-20 hydroxy group with $R"X^2$, in which $X^2$ is a leaving group, such as halogen (Cl, Br or I) or p-toluenesulphonyloxy or methanesulphonyloxy in the presence of base (e.g. KH) with or without catalyst (e.g. 18-Crown-6).
c  Acylation of the C-20 hydroxy groups with an acid halide in a suitable dry solvent (e.g. dichloromethane) in the presence of a base (e.g. triethylamine or pyridine) with or without catalyst (e.g. DMAP).
d  Optional functional group modification in the side chain.
e  Isomerization from "trans" to "cis" by means of UV-light in the presence of a triplet sensitizer, e.g. anthracene.
f  Deprotection of the alcohol groups by HF.
g  Deprotection of silyl ether protected alcohol groups with TBAF.
h  Deprotection of the THP-protected alcohol group in the side chain with PPTS.

The Grignard reagents $RMgX^1$, used in step a in Scheme 1, are prepared from the side chain fragments $RX^1$, which are either known compounds (several are described in International patent application number PCT/DK89/00079) or ay be prepared analogously to those described in PCT/DK89/00079.

The anions R⁻, derived from the side chain building blocks RH (see Scheme 1), can be obtained from the side chain building blocks containing an acidic hydrogen atom, e.g. compounds of formula VI, by treatment with e.g. alkyl-lithium or a Grignard reagent

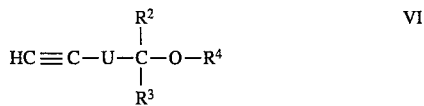

As a non-limiting illustration, the preparation of some compounds of the general formula VI where $U=(CH_2)_n$ ($n=0-3$) and $R^4=Si(CH_3)_3$ or THP is outlined in Scheme 2, but similar compounds of formula VI may be prepared by analogous methods. Some specific building blocks (RH) are listed in Table 1 and their synthesis are described in the preparations.

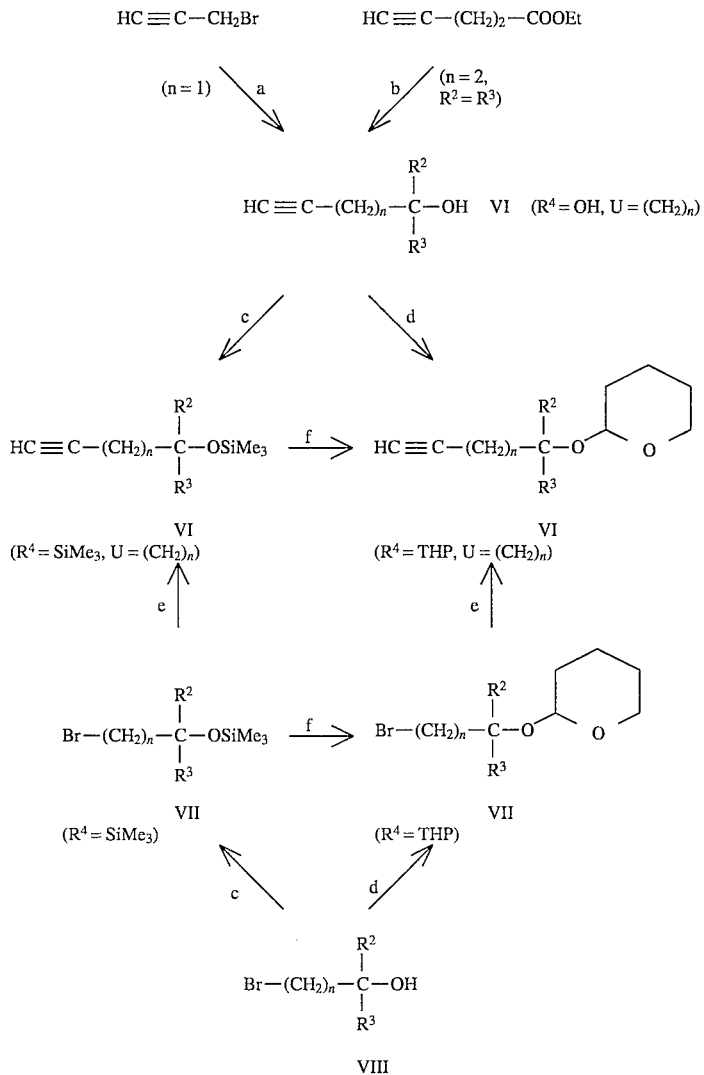

Scheme 2
Synthesis of some Side Chain Building Blocks VI

Notes to Scheme 2 a  (i) Al, (ii) $R^2R^3C=O$;
b  Grignard reagent $R^2MgBr$ or $R^2MgI$;
c  Me$_3$SiCl/base;
d  dihydropyran/acid;
e  acetylene/Na/liq.NH$_3$;
f  MeOH/acid, (ii) dihydropyran/acid.

TABLE 1

Some Side Chain Building Blocks, RH of General Formula VI

| Prep. Number | Compound Number | General Procedure | RH |
|---|---|---|---|
| 7 | 8 | 4 | H—≡—⟨—OSi(—)₃ (trimethylsilyloxy-dimethyl propargyl) |
| 8 | 9 | 2 | H—≡—CH₂—C(CH₃)₂—O—THP |
| 2 | 3 | 2 | H—≡—CH₂—C(Et)₂—O—THP |
| 10 | 11 | 2 | H—≡—CH₂CH₂—C(CH₃)₂—O—THP |
| 4 | 5 | 2 | H—≡—CH₂CH₂—C(Et)₂—O—THP |
| 6 | 7 | 6 | H—≡—CH₂CH₂CH₂—C(Et)₂—O—THP |

Intermediates for the preparation of the side chain building blocks, RH of Table 1, are either known compounds or can e.g. be prepared from the compounds listed in Table 2. The syntheses of these compounds are described in the Preparations.

TABLE 2

Some Intermediates for the Synthesis of RH (VI) of Table 1

| Type | Prep. No. | Compound No. | General Procedure | Formula |
|---|---|---|---|---|
| VI | 1 | 2 | 1 | H—≡—C(Et)₂—OH |
| VI | 9 | 10 | 3 | H—≡—CH₂—C(CH₃)₂—OH |
| VI | 3 | 4 | 3 | H—≡—CH₂—C(Et)₂—OH |

TABLE 2-continued

Some Intermediates for the Synthesis of RH (VI) of Table 1

| Type | Prep. No. | Compound No. | General Procedure | Formula |
|------|-----------|--------------|-------------------|---------|
| VII | 5 | 6 | 5 |  |

Addition of a reagent containing a nucleophilic carbon species (e.g. $R^-$ or Grignard reagent $RMgX^1$ (see Scheme 1) to the carbonyl group in 1 gives the alcohol II as a mixture of its two C-20 epimers. The ratio between the two epimeric forms depends on the reaction conditions and on the type of side chain building block used, but one of the epimers is usually formed in much higher yield than the other. This major epimer is by analogy with the product of similar reactions assumed to be the 20-R form in compounds where the C-22 carbon atom has a higher order of preference according to the Cahn, Ingold, Prelog-Rule than the C-17 carbon atom (e.g. compound 101 in Table 8) and the 20-S form in compounds where C-22 has a lower preference than C-17 (e.g. compound 108 in Table 8). Although the absolute configuration at the 20-position has not been proven, the terms 20-R and 20-S are used throughout this disclosure to characterize the two isomers. The two C-20-epimers of II may easily be separated (e.g. by chromatography), or the separation may be performed on a suitable later step in the synthesis.

The alkylation or acylation of the C-20-hydroxy compounds (II or IV) to yield the corresponding compounds of formula III or V can be performed by standard methods using conditions suitable for reactions with sterically hindered alcohols.

Tables 3, 4, 5, 6, and 7 contain non-limiting illustrations of compounds of formula II, III, IV, V, X, and XI, respectively. In addition to the steps shown in Scheme 1, one or more modification steps may be necessary. Thus, the group R in the compounds II, III, IV, V, X, and XI does not necessarily have the same meaning along a particular synthetic sequence. The conversion of R to $Q-U-C-(R^2)(R^3)Z$ may well involve several steps and possibly involve a temporary protection of the sensitive triene system of the molecule. Apart from any necessary modifications within the side chain, the conversion of II to I involves a photoisomerisation step and a deprotection step, analogous to the steps used in the last stages of the synthesis of other vitamin D a analogues (See European Patent No. 0 227 836).

Exemplified compounds of formula I of this invention are listed in Table 8.

TABLE 3

Non-limiting examples of intermediates of formula II

| Prep. No. | Compound No. | General Procedure | Stereo-chemistry | R |
|-----------|--------------|-------------------|------------------|---|
| 11 | 12 | 7 | 20R | 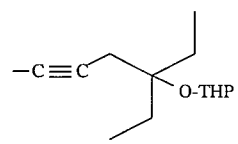 |
| 11 | 13 | 7 | 20S | 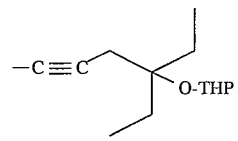 |
| 12 | 14 | 7 | 20R | 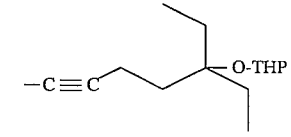 |
| 13 | 15 | 7 | 20R | 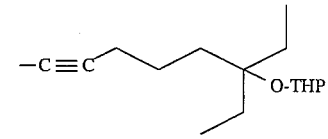 |

TABLE 3-continued

Non-limiting examples of intermediates of formula II

| Prep. No. | Compound No. | General Procedure | Stereo- chemistry | R |
|---|---|---|---|---|
| 18 | 20 | 10 | 20S | (structure with OSi(CH$_3$)$_3$) |
| 19 | 21 | 10 | 20S | (structure with OSi(CH$_3$)$_3$) |
| 20 | 22 | 10 | 20S | (structure with OSi(CH$_3$)$_3$) |
| 21 | 23 | 10 | 20S | (structure with OSi(CH$_3$)$_3$) |
| 22 | 24 | 10 | 20S | (structure with OSi(CH$_3$)$_3$) |
| 46 | 48 | 10 | 20S | (structure with OSi(CH$_3$)$_3$) |
| 47 | 49 | 10 | 20S | (structure with OSi(CH$_3$)$_3$) |
| 60 | 62 | 10 | 20S | (branched alkyl structure) |

TABLE 4

Non-limiting examples of intermediates of formula III

| Prep. No. | Compound No. | General Procedure | Stereo- chemistry | R" | R |
|---|---|---|---|---|---|
| 23 | 25 | 9 | 20R | —CH$_2$CH$_3$ | (—C≡C— structure with tetrahydropyranyl ether) |
| 24 | 26 | 9 | 20R | —CH$_3$ | (—C≡C— structure with tetrahydropyranyl ether) |
| 25 | 27 | 9 | 20S | —CH$_3$ | (structure with OSi(CH$_3$)$_3$) |

TABLE 4-continued
Non-limiting examples of intermediates of formula III
| Prep. No. | Compound No. | General Procedure | Stereo-chemistry | R" | R |
|---|---|---|---|---|---|
| 26 | 28 | 9 | 20S | —CH$_3$ | |
| 27 | 29 | 9 | 20S | —CH$_2$CH$_3$ | |
| 48 | 50 | 9 | 20S | —CH$_3$ | |
| 49 | 51 | 9 | 20S | —CH$_3$ | |
| 50 | 52 | 9 | 20S | —CH$_3$ | |
| 51 | 53 | 9 | 20S | —CH$_2$CH$_3$ | |
| 59 | 61 | 14 | 20S | —SOCH$_3$ | |
| 62 | 64 | 9 | 20S | —CH$_3$ | |
TABLE 5
Non-limiting examples of intermediates for formula IV
| Prep. No. | Compound No. | General Procedure | Stereo-chemistry | R |
|---|---|---|---|---|
| 14 | 16 | 8 | 20R | 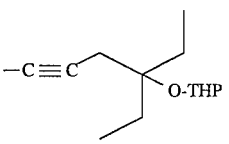 |

TABLE 5-continued
Non-limiting examples of intermediates for formula IV
| Prep. No. | Compound No. | General Procedure | Stereo-chemistry | R |
|---|---|---|---|---|
| 15 | 17 | 8 | 20S | 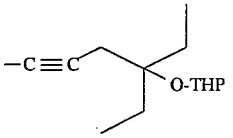 |
| 16 | 18 | 8 | 20R | 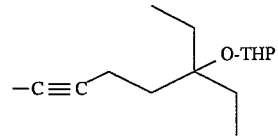 |
| 17 | 19 | 8 | 20R | 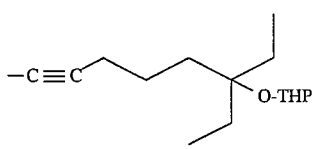 |
| 28 | 30 | 8 | 20S | 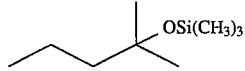 |
| 29 | 31 | 8 | 20S | 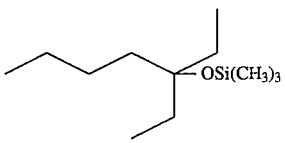 |
| 30 | 32 | 8 | 20S | 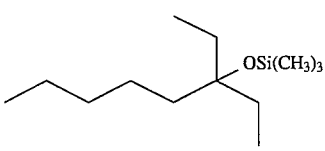 |
| 31 | 33 | 8 | 20S | 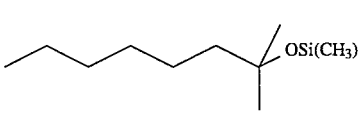 |
| 32 | 34 | 8 | 20S | 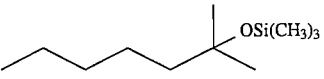 |
| 53 | 55 | 8 | 20S | 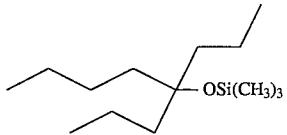 |
| 55 | 57 | 8 | 20S | 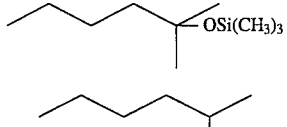 |
| 61 | 63 | 8 | 20S | 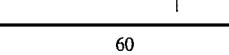 |

TABLE 6

Non-limiting examples of intermediates of formula V

| Prep. No. | Compound No. | General Procedure | Stereo-chemistry | R" | R |
|---|---|---|---|---|---|
| 33 | 35 | 8 | 20R | —CH$_2$CH$_3$ | —C≡C—CH$_2$—C(Et)$_2$—O—(tetrahydropyranyl) |
| 34 | 36 | 8 | 20R | —CH$_3$ | —C≡C—CH$_2$—C(Et)$_2$—O—(tetrahydropyranyl) |
| 35 | 37 | 8 | 20S | —CH$_3$ | butyl-C(Et)$_2$—OSi(CH$_3$)$_3$ |
| 36 | 38 | 8 | 20S | —CH$_3$ | hexyl-C(CH$_3$)$_2$—OSi(CH$_3$)$_3$ |
| 37 | 39 | 8 | 20S | —CH$_2$CH$_3$ | butyl-C(Et)$_2$—OSi(CH$_3$)$_3$ |
| 38 | 40 | 9 | 20R | —CH$_3$ | —C≡C—CH$_2$—C(Et)$_2$—O—(tetrahydropyranyl) |
| 52 | 54 | 8 | 20S | —SOCH$_3$ | butyl-C(Et)$_2$—OSi(CH$_3$)$_3$ |
| 54 | 56 | 8 | 20S | —CH$_3$ | dibutyl-C(propyl)—OSi(CH$_3$)$_3$ |
| 56 | 58 | 8 | 20S | —CH$_3$ | hexyl-C(CH$_3$)$_2$—OSi(CH$_3$)$_3$ |
| 57 | 59 | 8 | 20S | —CH$_3$ | hexyl-C(Et)$_2$—OSi(CH$_3$)$_3$ |

TABLE 6-continued

Non-limiting examples of intermediates of formula V

| Prep. No. | Compound No. | General Procedure | Stereo-chemistry | R" | R |
|---|---|---|---|---|---|
| 58 | 60 | 8 | 20S | —CH$_2$CH$_3$ | (structure with OSi(CH$_3$)$_3$) |
| 63 | 65 | 8 | 20S | —CH$_3$ | (branched alkyl structure) |

TABLE 7

Non-limiting examples of intermediates of formula X and XI

| Prep. No. | Compound No. | General Procedure | Stereo-chemistry | R" | R |
|---|---|---|---|---|---|
| 39 | 41 | 11 | 20R | H— | —C≡C— (structure with O-THP) |
| 40 | 42 | 11 | 20S | H— | —C≡C— (structure with O-THP) |
| 41 | 43 | 11 | 20R | H— | —C≡C— (structure with O-THP) |
| 42 | 44 | 11 | 20R | H— | —C≡C— (structure with O-THP) |
| 43 | 45 | 11 | 20R | CH$_3$CH$_2$— | —C≡C— (structure with O-THP) |
| 44 | 46 | 11 | 20R | CH$_3$— | —C≡C— (structure with O-THP) |

TABLE 7-continued

| | | Non-limiting examples of intermediates of formula X and XI | | | |
|---|---|---|---|---|---|
| Prep. No. | Compound No. | General Procedure | Stereo- chemistry | R" | R |
| 45 | 47 | 11 | 20R | $CH_3-$ | $-C{\equiv}C-\!\!\!-\!\!\!\diagdown\!\!\!-\!\!\!\diagup\!\!\!\!O\text{-THP}$ |

TABLE 8

| | | | Exemplified Compounds of General Formula I | | | | | | |
|---|---|---|---|---|---|---|---|---|---|
| Ex. No. | Compound No. | General Procedure | Stereo- chemistry | $R^1$ | Q | U | $R^2$ | $R^3$ | Z |
| 1 | 101 | 12 | 20R | H | $-C{\equiv}C-$ | $-CH_2-$ | Et | Et | OH |
| 2 | 102 | 12 | 20S | H | $-C{\equiv}C-$ | $-CH_2-$ | Et | Et | OH |
| 3 | 103 | 12 | 20R | Me | $-C{\equiv}C-$ | $-CH_2-$ | Et | Et | OH |
| 4 | 104 | 12 | 20R | Et | $-C{\equiv}C-$ | $-CH_2-$ | Et | Et | OH |
| 5 | 105 | 12 | 20R | H | $-C{\equiv}C-$ | $-(CH_2)_2-$ | Et | Et | OH |
| 6 | 106 | 12 | 20R | Me | $-C{\equiv}C-$ | $-(CH_2)_2-$ | Et | Et | OH |
| 7 | 107 | 12 | 20R | H | $-C{\equiv}C-$ | $-(CH_2)_3-$ | Et | Et | OH |
| 8 | 108 | 11 | 20S | H | $-CH_2-$ | $-CH_2-$ | Me | Me | OH |
| 9 | 109 | 11 | 20S | H | $-CH_2-$ | $-(CH_2)_2-$ | Et | Et | OH |
| 10 | 110 | 11 | 20S | Me | $-CH_2-$ | $-(CH_2)_2-$ | Et | Et | OH |
| 11 | 111 | 11 | 20S | Et | $-CH_2-$ | $-(CH_2)_2-$ | Et | Et | OH |
| 12 | 112 | 11 | 20S | H | $-CH_2-$ | $-(CH_2)_3-$ | Me | Me | OH |
| 13 | 113 | 11 | 20S | Me | $-CH_2-$ | $-(CH_2)_3-$ | Me | Me | OH |
| 14 | 114 | 11 | 20S | H | $-CH_2-$ | $-(CH_2)_3-$ | Et | Et | OH |
| 15 | 115 | 13 | 20S | H | $-CH_2-$ | $-(CH_2)_4-$ | Me | Me | OH |
| 16 | 116 | 11 | 20S | $CH_3SO-$ | $-CH_2-$ | $-(CH_2)_2-$ | Et | Et | OH |
| 17 | 117 | 11 | 20S | H | $-CH_2-$ | $-(CH_2)_2-$ | Pr | Pr | OH |
| 18 | 118 | 11 | 20S | Me | $-CH_2-$ | $-(CH_2)_2-$ | Pr | Pr | OH |
| 19 | 119 | 11 | 20S | H | $-CH_2-$ | $-(CH_2)_2-$ | Me | Me | OH |
| 20 | 120 | 11 | 20S | Me | $-CH_2-$ | $-(CH_2)_2-$ | Me | Me | OH |
| 21 | 121 | 11 | 20S | Me | $-CH_2-$ | $-(CH_2)_3-$ | Et | Et | OH |
| 22 | 122 | 11 | 20S | Et | $-CH_2-$ | $-(CH_2)_3-$ | Et | Et | OH |
| 23 | 123 | 11 | 20S | H | $-CH_2-$ | $-(CH_2)_2-$ | Me | Me | H |
| 24 | 124 | 11 | 20S | Me | $-CH_2-$ | $-(CH_2)_2-$ | Me | Me | H |
| | 125 | 11 | 20S | H | $-CH{=}CH-$ | $-CH_2-$ | Et | Et | OH |
| | 126 | 11 | 20S | H | $-CH_2-$ | $-(CH_2)_2-$ | Et | Me | OH |
| | 127 | 11 | 20S | Et | $-CH_2-$ | $-(CH_2)_2-$ | Et | Me | OH |

The present compounds are intended for use in pharmaceutical compositions which are useful in the treatment of human and veterinary disorders as described above.

The amount required of a compound of formula I (hereinafter referred to as the active ingredient) for therapeutic effect will, of course, vary both with the particular compound, the route of administration and the mammal under treatment. The compounds of the invention can be administered by the parenteral, intra-articular, enteral or topical routes. They are well absorbed when given enterally and this is the preferred route of administration in the treatment of systemic disorders. In the treatment of dermatological disorders like psoriasis or eye diseases topical or enteral forms are preferred.

In the treatment of respiratory diseases like asthma an aerosol is preferred.

While it is possible for an active ingredient to be administered alone as the raw chemical, it is preferable to present it as a pharmaceutical formulation. Conveniently, the active ingredient comprises from 0.1 ppm to 0.1% by weight of the formulation.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations, both for veterinary and for human medical use, of the present invention comprise an active ingredient in association with a pharmaceutically acceptable carrier therefore and optionally other therapeutic ingredient(s). The carrier(s) must be "acceptable" in the sense of being compatible with the other ingredients of the formulations and not deleterious to the recipient thereof.

The formulations include e.g. those in a form suitable for oral, rectal, parenteral (including subcutaneous, intramuscular and intravenous), intra-articular and topical administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

A tablet may be made by compressing or moulding the active ingredient optionally with one or more accessory ingredients. Compressed tablets may be prepared by compressing, in a suitable machine, the active ingredient in a free-flowing form such as a powder or granules, optionally mixed by a binder, lubricant, inert diluent, surface active or dispersing agent. Moulded tablets may be made by moulding, in a suitable machine, a mixture of the powdered active ingredient and suitable carrier moistened with an inert liquid diluent.

Formulations for rectal administration may be in the form of a suppository incorporating the active ingredient and a carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops.

For asthma treatment inhalation of powder, self-propelling or spray formulations, dispensed with a spray can, a nebulizer or an atomizer can be used. The formulations, when dispensed, preferably have a particle size in the range of 10 to 100µ.

Such formulations are most preferably in the form of a finely comminuted powder for pulmonary administration from a powder inhalation device or self-propelling powder-dispensing formulations. In the case of self-propelling solution and spray formulations, the effect may be achieved either by choice of a valve having the desired spray characteristics (i.e. being capable of producing a spray having the desired particle size) or by incorporating the active ingredient as a suspended powder in controlled particle size. These self-propelling formulations may be either powder-dispensing formulations or formulations dispensing the active ingredient as droplets of a solution or suspension.

Self-propelling powder-dispensing formulations preferably comprise dispersed particles of solid active ingredients, and a liquid propellant having a boiling point below 18° C. an atmospheric pressure. The liquid propellant may be any propellant known to be suitable for medicinal administration and may comprise one or more $C_1$–$C_6$-alkyl hydrocarbons or halogenated $C_1$–$C_6$-alkyl hydrocarbons or mixtures thereof; chlorinated and fluorinated $C_1$–$C_6$-alkyl hydrocarbons are especially preferred. Generally, the propellant constitutes 45 to 99.9% w/w of the formulation whilst the active ingredient constitutes 0.1 ppm to 0.1% w/w, of the formulation.

In addition to the aforementioned ingredients, the formulations of this invention may include one or more additional ingredients such as diluents, buffers, flavouring agents, binders, surface active agents, thickeners, lubricants, preservatives, e.g. methyl hydroxybenzoate (including antioxidants), emulsifying agents and the like.

The compositions may further contain other therapeutically active compounds usually applied in the treatment of the above mentioned pathological conditions.

The present invention further concerns a method for treating patients suffering from one of the above pathological conditions, said method consisting of administering to a patient in need of treatment an effective amount of one or more compounds of formula I, alone or in combination with one or more other therapeutically active compounds usually applied in the treatment of said pathological conditions. The treatment with the present compounds and/or with further therapeutically active compounds may be simultaneous or with intervals.

In the treatment of systemic disorders daily doses of from 0.1–100 µg, preferably from 0.2–25 µg, of a compound of formula I are administered. In the topical treatment of dermatological disorders, ointments, creams or lotions containing from 0.1–500 µg/g, and preferably from 0.1–100 µg/g, of a compound of formula I are administered. For topical use in ophthalmology ointments, drops or gels containing from 0.1–500 µg/g, and preferably from 0.1–100 µg/g, of a compound of formula I are administered. The oral compositions are formulated, preferably as tablets, capsules, or drops, containing from 0.05–50 µg, preferably from 0.1–25 µg, of a compound of formula I, per dosage unit.

The invention will now be further described in the following non-limiting General Procedures, Preparations and Examples:

GENERAL PROCEDURES, PREPARATIONS AND EXAMPLES

General

The exemplified compounds I are listed in Table 8.

For nuclear magnetic resonance spectra (300 MHz) chemical shift values ($\delta$) are quoted for deuteriochloroform solutions relative to internal tetramethylsilane ($\delta=0$) or chloroform ($\delta=7.25$). The value for a multipict, either defined (doublet (d), triplet (t), quartet (q)) or not (m) at the approximate mid point is given unless a range is quoted (s=singlet, b=broad). Coupling constants (J) are given in Hertz, and are sometimes approximated to the nearest unit.

Ether is diethyl ether, and was dried over sodium. THF was dried over sodium-benzophenone. Petroleum ether refers to the pentans fraction. Reactions were run at room temperature unless otherwise noted. The work-up procedure referred to involves dilution with the specified solvent (otherwise the organic reaction solvent), extraction with water and then brine, drying over anhydrous $MgSO_4$, and concentration in vacuo to give a residue. Chromatography was performed on silica gel.

GENERAL PROCEDURES

General Procedure 1: Reaction of ketones $R^2R^3C=O$ with organometallic reagent prepared from propargylbromide and aluminium to give the corresponding tertiary alcohol VI (Scheme 2, Table 2) (Preparation 1)

A mixture of aluminium scales (3.6 g), mercuric chloride (0.1 g) and dry THF (20 ml) was stirred at 20° C. for 20 minutes, under argon. A solution of propargyl bromide (23.8 g) in dry THF (20 ml) was added with stirring during 40 minutes, keeping the temperature at 25°–30° C. by intermittent cooling. The reaction mixture was stirred at 40°–45° C., heating as necessary, for 30 minutes. After cooling to about 25° C., a solution of the appropriate ketone, $R^2R^3C=O$ (0.2 mol) in dry ether (25 ml) was added during one hour, with stirring, cooling slightly to keep the temperature at about 25° C. Stirring was continued for a further half hour at 30°–35° C., after which the reaction mixture was worked up (ether). The residue was purified by distillation in vacuo through a 50 cm Podbielniak column to yield the title compound of the preparation as an oil.

General Procedure 2: Protection of tertiary alcohols VI or VII to give the corresponding 2-tetrahydropyranyl Compounds VI or VII (Scheme 2, Table 1) (Preparations 2, 3, 8 and 10)

A mixture of the appropriate compound VII or VII (0.01 mol), 3,4-dihydro-2H-pyran (1.26 g), PPTS (0.25 g) and dry dichloromethane (25 ml) was stirred under argon for 4 hours at 20° C. To the reaction mixture was added 100 ml of ether and 50 ml of semi-saturated aqueous sodium chloride solution. The organic phase was separated, dried and evaporated in vacuo to yield a crude product which was purified by chromatography (mixture of ether and pet.ether as eluant) to yield the title compound of the preparation.

General Procedure 3: Reaction of 4-pentinoic acid ethyl[1] ester with Grignard reagents, $R^2MgX^2$, to give the corresponding tertiary alcohol VI (Scheme 2, Table 2) (Preparations 3 and 9) ($X^1$=Cl, Br, I)

[1] an equimolar amount of a corresponding other lower alkyl ester, e.g. the methyl or propyl ester may be used instead of the ethyl ester.

To 1.1 g magnesium turnings (Grignard quality) in a dry flask, was added dropwise with stirring a solution of the appropriate alkyl halogenide $R^2X^1$ (0.045 mol) in dry ether (20 ml). The reaction took place under argon, with stirring, and with reflux, and lasted 20 minutes. Stirring and reflux was continued for a further 10 minutes.

This Grignard reagent was transferred to an addition funnel, under argon, and added dropwise with stirring and cooling to about −20° C., to a solution of 4-pentinoic acid ethyl[1] ester (1.9 g) in dry ether (20 ml). The addition lasted 15 minutes, and after that stirring was continued for 20 minutes at −20° C. and for one hour at 30° C.

The reaction mixture was poured into a mixture of 100 g ice/water and 4N hydrochloric acid (15 ml) under stirring. After addition of aqueous sodium bicarbonate solution to render a pH of circa 5, the mixture was extracted twice with ether (25 ml each). The combined organic phases were washed with water and saturated aqueous sodium chloride solution, dried and evaporated in vacuo to yield a crude product. This was purified either by distillation in vacuo or by chromatography (mixture of ether and pet.ether as eluant) to yield the title compound of the preparation.

[1] an equimolar amount of a corresponding other lower alkyl ester, e.g. the methyl or propyl ester may be used instead of the ethyl ester.

General Procedure 4: Protection of tertiary alcohols VI or VII to give the corresponding $A^1A^2A^3$ silyl Compound VI or VII (Scheme 2, Table 1) (Preparation 7)

To solution of the appropriate compound VII or VIII (14 mM) in a suitable dry solvent, e.g. dichloromethane or DMF, was added one or more suitable base(s), e.g. triethylamine, DMAP or imidazole, under argon and with stirring and cooling in an ice bath. A suitable silylating agent, $A^1A^2A^3SiX^2$, e.g. TMSCl, TBDMSOTf triethylsilyltriflate or diphenylmethylsilyl chloride, was added dropwise with stirring during 20 minutes at 0° C. Stirring was continued for a sufficient time (typically for 0.5 to 24 hours) at a suitable temperature (typically 25° C. to 50° C.). After a suitable work-up the crude product was purified by chromatography to yield the title compound of the preparation.

General Procedure 5: Conversion of TMS-protected alcohols of type VI or VII to the corresponding THP-protected compound of type VI or VII (Scheme 2, Table 2) (Preparation 5)

To a solution of the appropriate TMS-protected tertiary alcohol VI or VII (0.02 mol) in methanol (25 ml) was added 5 drops of 6M hydrogen chloride in methanol and the mixture was stirred for 15 minutes at 20° C. The reaction mixture was evaporated until the methanol was removed, and the residue was redissolved in dichloromethane (40 ml). To this solution was added 3,4-dihydro-2-H-pyran (3.3 g) and PPTS (0.16 g) in portions under stirring and cooling in an ice-bath. After that, the mixture was stirred at 20° C. for three hours and then diluted with ether (200 ml). The ether phase was extracted with saturated aqueous sodium bicarbonate, water and saturated aqueous sodium chloride, dried and evaporated in vacuo to yield a crude product. This was purified by chromatography (mixture of ether and pet.ether as eluant) to yield the title compound of the preparation as an oil.

General Procedure 6: Conversion of Compounds VII, with a terminal bromine atom, to the corresponding Compound VI, with a terminal ethinyl group (Scheme 2, Table 1) (Preparation 6)

Through dry liquid ammonia (circa 75 ml) dry acetylene was bubbled at a rate of about 200 ml per minute with stirring. At the same time sodium (0.5 g) was added in small pieces during 5 minutes. After about 5 minutes more, the flow of acetylene was discontinued, and the appropriate bromo-compound VII (3 mmol) was added during 5 minutes; stirring at room temperature was continued until all of the ammonia had evaporated (2 to 4 hours). Pet.ether (100 ml) and ice/water (100 g) was added under stirring. The organic phase was separated, washed several times with water until neutral, dried and evaporated in vacuo to yield a crude product. This was purified by chromatography (dichloromethane or mixture of dichloromethane and pet.ether as eluants) to yield the title compound of the preparation.

General Procedure 7: Reaction of Compound 1 with side chain building blocks VI (RH) to yield Compound II (Scheme 1, Table 3) (Preparations 11–13)

To a solution of the appropriate compound VI (1.5 mmol) in dry THF (5 ml), cooled to −70° C. and stirred under argon, was added dropwise, during 2 minutes, a solution of n-butyllithium (1.6 mM in hexane; 0.65 ml). Stirring was continued at −70° C. for 10 minutes and then at 20° C. for one hour. The mixture was again cooled to −70° C., and a solution of the ketone, compound 1 (0.28 g; 0.5 mmole) in dry THF (5 ml) was added dropwise, during 4 minutes, and after that, stirring was continued at −70° C. for 30 minutes. The reaction mixture was worked up (ether) to yield a crude product which was purified by means of chromatography (mixture of ether and pet.ether as eluant) to yield the title compound(s) of the preparation.

General Procedure 8: Isomerization of Compounds II or III to the corresponding compound IV or V (Scheme 1, Table 5 and 6) (Preparations 14–17, 28–37, 52–58, 61 and 63)

A solution of the appropriate compound II or III (0.3 mmol), anthracene (100 mg) and triethylamine (0.05 ml) in dichloromethane (20 ml) under argon in a Pyrex flask was irradiated with UV-light from a high pressure ultraviolet lamp, type TQ760Z2 (Hanau) at about 10° C. for 20 minutes under stirring. The reaction mixture was concentrated in vacuo and treated with pet.ether (2×5 ml). After filtering the filtrate was concentrated in vacuo and purified by chromatography (mixture of ether and pet.ether as eluant) to yield the title compound of the preparation or example.

General Procedure 9: Alkylation of a C-20-hydroxy compound of type II to the corresponding compound of type III (Scheme 1, Tables 4 and 6) (Preparations 23–27, 38, 48–51 and 62)

To a solution of the appropriate compound II (0.5 mmol) in dry THF (5 ml), a 20% suspension of potassium hydride in mineral oil (0.2 ml) was added while stirring at 20° C. under argon. Then, a solution of 18-Crown-6 (0.13 g) in dry THF (2 ml) was added during 5 minutes followed by an alkylating agent R"X$^2$ (1.5 mmol). Stirring at 20° C. was continued for 6–24 hours after which the reaction mixture was worked up (ether). The crude product was purified by chromatography (mixture of ether and pet.ether as eluant) to yield the title compound of the preparation.

General Procedure 10: Reaction of Compound 1 with a Grignard reagent R-MgX$^1$ to yield Compound II (Scheme 1, Table 3) (Preparations 18–22, 46–47 and 60)

Magnesium turnings (35 mmol) suspended in a 2:1 blend of dry ether and dry THF (10 ml) under argon were stirred vigorously and heated to reflux temperature. A solution of the appropriate alkyl halogenide RX$^1$ (34 mmol) dissolved in a 2:1 blend of dry ether and dry THF (100 ml) was added dropwise over 45 minutes and refluxed for a further 60 minutes.

The reaction mixture was cooled to room temperature (20° C.) and a solution of compound 1 (1.99 g, 3.4 mmol) in dry ether/dry THF 2:1 (40 ml) was added during 15 minutes. The reaction blend was then heated to reflux, refluxed for 1 hour, cooled to room temperature and worked up (ether) to yield a crude product which was purified by chromatography (mixture of ether and pet.ether as eluant) to yield the title compound of the preparation.

General Procedure 11: Deprotection of Compounds IV or V to the corresponding Compounds X, XI or I by treatment with tetra-n-butylammonium fluoride (Scheme 1, Table 7) (Preparations 39–45 and Examples 8–14 and 16–24)

To a solution of the appropriate compound IV or V (0.16 mmol)) in THF (5 ml), a solution of TBAF (300 mg) in THF (5 ml) was added while stirring at 60° C. under argon. Stirring was continued for one hour at 60° C., and the reaction mixture was worked up (ether acetate with an additional extraction with "NaHCO$_3$" before the extractions in the work-up procedure). The residue was purified by chromatography (0% to 50% pet.ether in ethyl acetate as eluant) to yield the title compound.

General Procedure 12: Deprotection of Compounds X and XI to the corresponding Compounds I by treatment with pyridinium toluene-4-sulphonate (Scheme 1, Table 8) (Example 1–7)

To a solution of the appropriate compound X or XI (0.16 mmol) in 99% ethanol (2 ml) PPTS (2 mg) was added, and the mixture was stirred at 50° C. under argon for one hour. After work-up (ethyl acetate, extraction with "NaHCO$_3$" before the extractions-in the work-up procedure), the crude product was purified by chromatography (0% to 50% pet.ether in ethyl acetate as eluant) to yield the title compound of the example.

General Procedure 13: Deprotection of Compounds IV or V to the corresponding Compound I by treatment with "HF" (Scheme 1, Table 8) (Example 15)

To a solution of the appropriate compound IV or V (0.07 mmol) in ethyl acetate (0.2 ml) was added acetonitrile (2 ml) followed by a 5% solution of hydrofluoric acid in acetonitrile:water, 7:1 (1.2 ml) under argon and with stirring. Stirring was continued for 45 minutes at 20° C. Saturated aqueous sodium bicarbonate solution (10 ml) was added, and the reaction mixture was worked up (ethyl acetate) The residue was purified by chromatography (ethyl acetate or a mixture of ethyl acetate and hexane or pentane as eluant) to yield the title compound of the example.

General Procedure 14: Acylation of a C-20 hydroxy compound of type II to the corresponding compound of type III (Scheme 1, Table 4, Preparation 59)

To a solution of the appropriate compound II (0.65 mmol) in dry pyridine cooled to 0° the acid halide R"X was added. The reaction mixture was stirred 30 minutes at 0° C. followed by 1 hour at 20° C. Then, the reaction mixture was worked up (ether), and the crude product was purified by chromatography (mixture of ether and pet.ether as eluant) to yield the title compound of the preparation.

Preparation 1: Compound 2

Method: General Procedure 1.

Starting material: Diethyl ketone.

B.p. of Compound 2: 71°–72° C./30 mbar.

NMR: δ=0.90 (t, 6H), 1.60 (m, 4H), 1.75 (s, 1H), 2.05 (t, 1H), 2.35 (m, 2H).

Preparation 2: Compound 3

Method: General Procedure 2.

Starting material: Compound 2.

Chromatography eluant: 0% to 5% ether in pet.ether.

NMR: δ=0.90 (m, 6H), 1.45–1.92 (m, 10H), 1.96 (t, 1H), 2.46 (d, 2H), 3.47 (m, 1H), 3.98 (m, 1H), 4.81 (m, 1H).

Preparation 3: Compound 4

Method: General Procedure 3.

Starting material: Ethyl magnesium bromide.

Chromatography eluant: 25% ether in pet.ether.

NMR: δ=0.87 (t, 6H), 1.48 (m, 4H), 1.71 (m, 2H), 1.97 (t, 2H), 2.26 (m, 2H).

Preparation 4: Compound 5

Method: General Procedure 2.

Starting material: Compound 4.

Chromatography eluant: 0% to 5% ether in pet.ether.

NMR: δ=1.21 (s, 3H), 1.23 (s, 3H), 1.51 (m, 4H), 1.64 (m, 1H), 1.78 (t, 2H), 1.83 (m, 1H), 1.92 (t, 1H), 2.29 (m, 2H), 3.45 (m, 1H), 3.93 (m, 1H), 4.73 (m, 1H).

Preparation 5: Compound 6

Method: General Procedure 5.

Starting material: 1-Bromo-4-ethyl-4-trimethylsilyloxy-hexane.

Chromatography eluant: 10% ether in pet.ether.

NMR: δ=0.83 (m, 6H), 1.45–2.05 (m, 14H), 3.43 (t, 2H), 3.45 (m, 1H), 3.94 (m, 1H), 4.68 (m, 1H).

Preparation 6: Compound 7

Method: General Procedure 6.

Starting material: Compound 6.

Chromatography eluant: Dichloromethane.

NMR: δ=0.83 (t, 6H), 1.54 (q, 4H), 1.45–1.90 (m, 10H), 1.95 (t, 1H), 2.17 (m, 2H), 3.44 (m, 1H), 3.95 (m, 1H), 4.69 (m, 1H).

Preparation 7: Compound 8

Method: General Procedure 4.
Starting material: 3-Ethyl-1-pentin-3-ol.
Solvent: Dichloromethane (20 ml).
Base: N-ethyl-diisopropylamine (2.0 g).
Silylating agent: Chlorotrimethylsilane (1.7 g).
Reaction temperature: 20° C.
Reaction time: 1 hour.
Work-up: Additional extraction with phosphate buffer (pH 6.5, 0.07M, 60 ml).
NMR: $\delta$=0.17 (s, 9H), 0.95 (t, 6H), 1.63 (q, 4H), 2.42 (s, 1H).

Preparation 8: Compound 9

Method: General Procedure 2.
Starting material: 1-Methyl-4-pentin-2-ol.
Chromatography eluant: 5% ether in pet.ether.
NMR: $\delta$=1.34 (s, 3H), 1.35 (s, 3H), 1.51 (m, 4H), 1.67 (m, 1H), 1.84 (m, 1H), 2.00 (t, 1H), 2.44 (m, 2H), 3.45 (m, 1H), 3.97 (m, 1H), 4.81 (m, 1H).

Preparation 9: Compound 10

Method: General Procedure 3.
Starting material: Methyl magnesium iodide.
Purification by distillation in vacuo.
Bp. of compound 20: 58°–59° C./12 mmHg.
NMR: $\delta$=1.24 (s, 6H), 1.69 (s, 1H), 1.75 (t, 2H), 1.98 (t, 1H), 2.31 (m, 2H).

Preparation 10: Compound 11

Method: General Procedure 2.
Starting material: Compound 10.
Chromatography eluant: 0% to 5% ether in pet.ether.
NMR: $\delta$=1.21 (s, 3H), 1.23 (s, 3H), 1.51 (m, 4H), 1.64 (m, 1H), 1.78 (t, 2H), 1.83 (m, 1H), 1.92 (t, 1H), 2.29 (m, 2H), 3.45 (m, 1H), 3.93 (m, 1H), 4.73 (m, 1H).

Preparation 11: Compounds 12 and 13

Method: General Procedure 7.
Starting material: Compound 3.
Chromatography eluant: 15% to 25% ether in pet.ether.
NMR 12: $\delta$=0.05 (m, 12H), 0.81 (s, 3H), 0.86 (s, 9H), 0.89 (s, 9H), 0.83–0.90 (m, 6H), 1.46 (bs, 3H), 1.27–2.07 (m, 23H), 2.15 (bd, 1H), 2.31 (bd, 1H), 2.45 (bs, 2H), 2.55 (dd, 1H), 2.86 (m, 1H), 3.44 (m, 1H), 3.95 (m, 1H), 4.21 (m, 1H), 4.53 (m, 1H), 4.79 (m, 1H), 4.93 (m, 1H), 4.98 (m, 1H), 5.80 (d, 1H), 6.45 (d, 1H).
NMR 13: $\delta$=0.05 (m, 12H), 0.72 (s, 3H), 0.86 (s, 9H), 0.89 (s, 9H), 0.80–0.92 (m, 6H), 1.48 (s, 3H), 1.15–2.25 (m, 24H), 2.31 (bd, 1H), 2.46 (s, 2H), 2.55 (dd, 1H), 2.87 (m, 1H), 3.45 (m, 1H), 3.96 (m, 1H), 4.21 (m, 1H), 4.53 (m, 1H), 4.79 (m, 1H), 4.94 (m, 1H), 4.98 (m, 1H), 5.82 (d, 1H), 6.45 (d, 1H).

Preparation 12: Compound 14

Method: General Procedure 7.
Starting material: Compound 7.
Eluant (chromatography): 20% ether in pet.ether.
NMR: $\delta$=0.06 (m, 12H), 0.86 (s, 9H), 0.89 (s, 9H), 0.77–0.94 (m, 9H), 1.45 (s, 3H), 1.15–2.45 (m, 29H), 2.52 (dd, 1H), 2.86 (m, 1H), 3.45 (m, 1H), 3.92 (m, 1H), 4.21 (m, 1H), 4.52 (m, 1H), 4.66 (m 1H), 4.93 (m, 1H), 4.98 (m, 1H), 5.82 (d, 1H), 6.45 (d, 1H).

Preparation 13: Compound 15

Method: General Procedure 7.
Starting material: Compound 7.
Chromatography eluant: 15% to 20% ether in pet.ether.
NMR: $\delta$=0.05 (m, 12H), 0.80 (bs, 3H), 0.82 (t, 6H), 0.86 (s, 9H), 0.88 (s, 9H), 1.45 (bs, 3H), 1.10–2.07 (m, 27H), 2.15 (m, 3H), 2.37 (bd, 1H), 2.48 (dd, 1H), 2.85 (bd, 1H), 3.44 (m, 1H), 3.93 (m, 1H), 4.20 (m, 1H), 4.50 (m, 1H), 4.70 (m, 1H), 4.91 (m, 1H), 4.98 (m, 1H), 5.81 (d, 1H), 6.44 (d, 1H).

Preparation 14: Compound 16

Method: General Procedure 8.
Starting material: Compound 12.
Chromatography eluant: 15% to 20% ether in pet.ether.
NMR: $\delta$=0.06 (m, 12H), 0.80 (s, 3H), 0.86 (s, 9H), 0.87 (s, 9H), 0.85–0.92 (m, 6H), 1.45 (bs, 3H), 1.25–2.05 (m, 23H), 2.07–2.27 (m, 2H), 2.43 (m 1H), 2.44 (s, 2H), 2.81 (m, 1H), 3.45 (m, 1H), 3.94 (m, 1H), 4.18 (m, 1H), 4.37 (m, 1H), 4.79 (m, 1H), 4.86 (m, 1H), 5.18 (m, 1H), 6.00 (d, 1H), 6.22 (d, 1H).

Preparation 15: Compound 17

Method: General Procedure 8.
Starting material: Compound 13.
Eluant (chromatography): 15% to 20% ether in pet.ether.
NMR: $\delta$=0.06 (m, 12H), 0.70 (s, 3H), 0.86 (s, 18H), 0.80–0.90 (m, 6H), 1.47 (s, 3H), 1.10–2.05 (m, 23H), 2.17 (bd, 1H), 2.21 (dd, 1H), 2.43 (dd, 1H), 2.45 (s, 2H), 2.82 (m, 1H), 3.45 (m, 1H), 3.95 (m, 1H), 4.18 (m, 1H), 4.37 (m, 1H), 4.79 (m, 1H), 4.85 (m, 1H), 5.18 (m, 1H), 6.01 (d, 1H), 6.22 (d, 1H).

Preparation 16: Compound 18

Method: General Procedure 8.
Starting material: Compound 14.
Eluant (chromatography): 15% ether in pet.ether.
NMR: $\delta$=0.05 (m, 12H), 0.79 (s, 3H), 0.81 (t, 6H), 0.87 (s, 9H), 0.88 (s, 9H), 1.44 (s, 3H), 1.25–2.35 (m, 29H), 2.44 (dd, 1H), 2.81 (m, 1H), 3.42 (m, 1H), 3.92 (m, 1H), 4.17 (m, 1H), 4.37 (m, 1H), 4.65 (m, 1H), 4.86 (m, 1H), 5.19 (m, 1H), 6.00 (d, 1H), 6.22 (d, 1H).

Preparation 17: Compound 19

Method: General Procedure 8.
Starting material: Compound 15.
Chromatography eluant: 12.5% ether in pet.ether.
NMR: $\delta$=0.06 (m, 12H), 0.79 (s, 3H), 0.81 (t, 6H), 0.86 (s, 9H), 0.87 (s, 9H), 1.45 (bs, 3H), 1.25–2.25 (m, 31H), 2.42 (dd, 1H), 2.81 (m, 1H), 3.43 (m, 1H), 3.93 (m, 1H), 4.17 (m, 1H), 4.38 (t, 1H), 4.70 (m, 1H), 4.86 (m, 1H), 5.19 (m, 1H), 6.00 (d, 1H), 6.21 (d, 1H).

Preparation 18: Compound 20

Method: General Procedure 10.

Starting material: 4-bromo-2-methyl-2-trimethylsilyl-oxy-butane.

Eluant (chromatography): 10% ether in pet.ether.

NMR: δ=0.05 (m, 12H), 0.12 (s, 9H), 0.72 (s, 3H), 0.85 (s, 9H), 0.89 (s, 9H), 1.20 (s, 3H), 1.22 (s, 3H), 1.24 (s, 3H), 1.10–2.20 (m, 18H), 2.29 (bd, 1H), 2.56 (dd, 1H), 2.86 (m, 1H), 4.21 (m, 1H), 4.53 (m, 1H), 4.94 (m, 1H), 4.98 (m, 1H), 5.82 (d, 1H), 6.45 (d, 1H).

Preparation 19: Compound 21

Method: General Procedure 10.

Starting material: 6-bromo-3-ethyl-3-trimethylsilyl-oxy-hexane.

Eluant (chromatography): 5% ether in pet.ether.

NMR: δ=0.05 (m, 12H), 0.09 (s, 9H), 0.71 (s, 3H), 0.80 (t, 6H), 0.85 (s, 9H), 0.89 (s, 9H), 1.28 (s, 3H), 1.46 (q, 4H), 1.15–2.15 (m, 20H), 2.29 (bd, 1H), 2.56 (dd, 1H), 2.87 (m, 1H), 4.21 (m, 1H), 4.53 (m, 1H), 4.94 (m, 1H), 4.99 (m, 1H), 5.82 (d, 1H), 6.45 (d, 1H).

Preparation 20: Compound 22

Method: General Procedure 10.

Starting material: 7-bromo-3-ethyl-3-trimethylsilyl-oxy-heptane.

Eluant (chromatography): 5% ether in pet.ether.

NMR: δ=0.06 (m, 12H), 0.08 (s, 9H), 0.71 (s, 3H), 0.80 (t, 6H), 0.85 (s, 9H), 0.89 (s, 9H), 1.27 (s, 3H), 1.44 (q, 4H), 1.10–2.15 (m, 22H), 2.29 (bd, 1H), 2.56 (dd, 1H), 2.86 (m, 1H), 4.21 (m, 1H), 4.53 (m, 1H), 4.94 (m, 1H), 4.98 (m, 1H), 5.82 (d, 1H), 6.45 (d, 1H).

Preparation 21: Compound 23

Method: General Procedure 10.

Starting material: 7-bromo-2-methyl-2-trimethylsilyl-oxy-heptane.

Eluant (chromatography): 2% to 5% ether in pet.ether.

NMR: δ=0.06 (m, 12H), 0.09 (s, 9H), 0.71 (s, 3H), 0.85 (s, 9H), 0.89 (s, 9H), 1.19 (s, 6H), 1.27 (s, 3H), 1.10–2.15 (m, 24H), 2.29 (bd, 1H), 2.56 (dd, 1H), 2.86 (m, 1H), 4.21 (m, 1H), 4.53 (m, 1H), 4.94 (m, 1H), 4.98 (m, 1H), 5.82 (d, 1H), 6.45 (d, 1H).

Preparation 22: Compound 24

Method: General Procedure 10.

Starting material: 6-bromo-2-methyl-2-trimethylsilyl-oxy-hexane.

Eluant (chromatography): 1% to 10% ether in pet.ether.

NMR: δ=0.05 (m, 12H), 0.10 (s, 9H), 0.71 (s, 3H), 0.85 (s, 9H), 0.89 (s, 9H), 1.18 (s, 6H), 1.26 (s, 3H), 1.00–2.15 (m, 22H), 2.29 (bd, 1H), 2.56 (dd, 1H), 2.86 (m, 1H), 4.21 (m, 1H), 4.53 (m, 1H), 4.93 (m, 1H), 4.98 (m, 1H), 5.81 (d, 1H), 6.44 (d, 1H).

Preparation 23: Compound 25

Method: General Procedure 9.

Starting materials: Compound 12 and ethyl iodide.

Eluant (chromatography): 0% to 10% ether in pet.ether.

NMR: δ=0.05 (m, 12H), 0.75 (s, 3H), 0.85 (s, 9H), 0.88 (s, 9H), 0.80–0.92 (m, 6H), 1.14 (t, 3H), 1.33 (s, 3H), 1.20–2.05 (m, 22H), 2.22 (bd, 1H), 2.31 (bd, 1H), 2.45 (m, 2H), 2.53 (dd, 1H), 2.83 (bd, 1H), 3.43 (m, 1H), 3.46 (m, 1H), 3.68 (m, 1H), 3.95 (m, 1H), 4.20 (m, 1H), 4.52 (m, 1H), 4.79 (m, 1H), 4.93 (m, 1H), 4.97 (m, 1H), 5.78 (d, 1H), 6.45 (d, 1H).

Preparation 24: Compound 26

Method: General Procedure 9.

Starting materials: Compound 12 and methyl iodide.

Eluant (chromatography): 0% to 10% ether in pet.ether.

NMR: δ=0.05 (m, 12H), 0.74 (s, 3H), 0.86 (s, 9H), 0.89 (s, 9H), 0.84–0.94 (m, 6H), 1.35 (s, 3H), 1.15–2.10 (m, 22H), 2.17 (bd, 1H), 2.32 (bd, 1H), 2.48 (m, 2H), 2.54 (dd, 1H), 2.85 (bd, 1H), 3.32 (s, 3H), 3.44 (m, 1H), 3.96 (m, 1H), 4.21 (m, 1H), 4.52 (m, 1H), 4.79 (m, 1H), 4.93 (m, 1H), 4.98 (m, 1H), 5.79 (m, 1H), 6.45 (m, 1H).

Preparation 25: Compound 27

Method: General Procedure 9.

Starting materials: Compound 21 and methyl iodide.

Eluant (chromatography): 2% ether in pet.ether. Crystallized from methanol.

M.p.: 92°–94° C.

NMR: δ=0.06 (m, 12H), 0.09 (s, 9H), 0.63 (s, 3H), 0.81 (t, 6H), 0.86 (s, 9H), 0.89 (s, 9H), 1.17 (s, 3H), 1.46 (q, 4H), 1.10–2.10 (m, 19H), 2.30 (bd, 1H), 2.55 (dd, 1H), 2.86 (m, 1H), 3.13 (s, 3H), 4.21 (m, 1H), 4.53 (m, 1H), 4.93 (m, 1H), 4.98 (m, 1H), 5.81 (d, 1H), 6.45 (d, 1H).

Preparation 26: Compound 28

Method: General Procedure 9.

Starting materials: Compound 24 and methyl iodide.

Eluant (chromatography): 1% to 2% ether in pet.ether.

NMR: δ=0.05 (m, 12H), 0.10 (s, 9H), 0.63 (s, 3H), 0.86 (s, 9H), 0.89 (s, 9H), 1.16 (s, 3H), 1.19 (s, 6H), 1.05–2.10 (m, 21H), 2.30 (bd, 1H), 2.55 (dd, 1H), 2.86 (m, 1H), 3.13 (s, 3H), 4.21 (m, 1H), 4.53 (m, 1H), 4.93 (m, 1H), 4.98 (m, 1H), 5.81 (d, 1H), 6.45 (d, 1H).

Preparation 27: Compound 29

Method: General Procedure 9.

Starting materials: Compound 21 and ethyl bromide.

Eluant (chromatography): 2% ether in pet.ether.

NMR: δ=0.06 (m, 12H), 0.09 (s, 9H), 0.64 (s, 3H), 0.81 (t, 6H), 0.86 (s, 9H), 0.89 (s, 9H), 1.10 (t, 3H), 1.18 (s, 3H), 1.46 (q, 4H), 1.00–2.10 (m, 19H), 2.32 (bd, 1H), 2.53 (dd, 1H), 2.86 (m, 1H), 3.32 (m, 2H), 4.21 (m, 1H), 4.52 (m, 1H), 4.93 (m, 1H), 4.98 (m, 1H), 5.81 (d, 1H), 6.45 (d, 1H).

Preparation 28: Compound 30

Method: General Procedure 8.

Starting material: Compound 20.

Eluant (chromatography): 1% to 4% ether in pet.ether.

NMR: δ=0.05 (m, 12H), 0.10 (s, 9H), 0.71 (s, 3H), 0.86 (s, 18H), 1.20 (s, 3H), 1.21 (s, 3H), 1.23 (s, 3H), 1.10–2.15 (m, 18H), 2.20 (bd, 1H), 2.44 (dd, 1H), 2.81 (m, 1H), 4.18 (m, 1H), 4.36 (m, 1H), 4.86 (m, 1H), 5.17 (m, 1H), 6.01 (d, 1H), 6.22 (d, 1H).

Preparation 29: Compound 31

Method: General Procedure 8.

Starting material: Compound 21.

Eluant (chromatography): 2% to 10% ether in pet.ether.

NMR: δ=0.05 (m, 12H), 0.09 (s, 9H), 0.70 (s, 3H), 0.80 (t, 6H), 0.86 (s, 9H), 0.87 (s, 9H), 1.27 (s, 3H), 1.46 (q, 4H), 1.15–2.15 (m, 20H), 2.21 (dd, 1H), 2.44 (dd, 1H), 2.81 (m, 1H), 4.18 (m, 1H), 4.36 (m, 1H), 4.85 (m, 1H), 5.17 (m, 1H), 6.01 (d, 1H), 6.22 (d, 1H).

Preparation 30: Compound 32

Method: General Procedure 8.

Starting material: Compound 22.

Eluant (chromatography): 0% to 5% ether in pet.ether.

NMR: δ=0.05 (m, 12H), 0.08 (s, 9H), 0.70 (s, 3H), 0.80 (t, 6H), 0.86 (s, 9H), 0.87 (s, 9H), 1.26 (s, 3H), 1.44 (q, 4H), 1.10–2.15 (m, 22H), 2.21 (dd, 1H), 2.44 (dd, 1H), 2.82 (m, 1H), 4.18 (m, 1H), 4.36 (m, 1H), 4.86 (m, 1H), 5.17 (m, 1H), 6.01 (d, 1H), 6.23 (d, 1H).

Preparation 31: Compound 33

Method: General Procedure 8.

Starting material: Compound 23.

Eluant (chromatography): 0% to 5% ether in pet.ether.

NMR: δ=0.05 (m, 12H), 0.09 (s, 9H), 0.70 (s, 3H), 0.86 (s, 9H), 0.87 (s, 9H), 1.19 (s, 6H), 1.26 (s, 3H), 1.10–2.15 (m, 24H), 2.21 (dd, 1H), 2.44 (dd, 1H), 2.81 (m, 1H), 4.18 (m, 1H), 4.37 (m, 1H), 4.86 (m, 1H), 5.17 (m, 1H), 6.01 (d, 1H), 6.22 (d, 1H).

Preparation 32: Compound 34

Method: General Procedure 8.

Starting material: Compound 24.

Eluant (chromatography): 0% to 5% ether in pet.ether.

NMR: δ=0.05 (m, 12H), 0.09 (s, 9H), 0.70 (s, 3H), 0.87 (s, 18H), 1.18 (s, 6H), 1.26 (s, 3H), 1.10–2.15 (m, 22H), 2.20 (dd, 1H), 2.44 (dd, 1H), 2.81 (m, 1H), 4.18 (m, 1H), 4.36 (m, 1H), 4.86 (m, 1H), 5.17 (m, 1H), 6.01 (d, 1H), 6.22 (d, 1H).

Preparation 33: Compound 35

Method: General Procedure 8.

Starting material: Compound 25.

Eluant (chromatography): 0% to 5% ether in pet.ether.

NMR: δ=0.05 (m, 12H), 0.74 (s, 3H), 0.87 (s, 9H), 0.88 (s, 9H), 0.82–0.92 (m, 6H), 1.15 (t, 3H), 1.33 (s, 3H), 1.10–2.05 (m, 22H), 2.20 (m, 2H), 2.44 (dd, 1H), 2.46 (s, 2H), 2.79 (bd, 1H), 3.44 (m, 1H), 3.49 (m, 1H), 3.69 (m, 1H), 3.96 (m, 1H), 4.18 (m, 1H), 4.37 (m, 1H), 4.79 (m, 1H), 4.86 (m, 1H), 5.18 (m, 1H), 5.99 (d, 1H), 6.23 (d, 1H).

Preparation 34: Compound 36

Method: General Procedure 8.

Starting material: Compound 26.

Eluant (chromatography): 0% to 10% ether in pet.ether.

NMR: δ=0.05 (m, 12H), 0.73 (s, 3H), 0.86 (s, 9H), 0.87 (s, 9H), 0.82–0.92 (m, 6H), 1.34 (s, 3H), 1.15–2.00 (m, 22H), 2.16 (bd, 1H), 2.20 (dd, 1H), 2.43 (dd, 1H), 2.53 (s, 2H), 2.79 (bd, 1H), 3.31 (s, 3H), 3.43 (m, 1H), 3.95 (m, 1H), 4.18 (m, 1H), 4.36 (m, 1H), 4.79 (m, 1H), 4.87 (m, 1H), 5.18 (m, 1H), 5.99 (d, 1H), 6.22 (d, 1H).

Preparation 35: Compound 37

Method: General Procedure 8.

Starting material: Compound 27.

Eluant (chromatography): 2% ether in pet.ether.

NMR: δ=0.05 (m, 12H), 0.10 (s, 9H), 0.62 (s, 3H), 0.81 (t, 6H), 0.87 (s, 9H), 0.88 (s, 9H), 1.16 (s, 3H), 1.46 (q, 4H), 1.10–2.10 (m, 19H), 2.21 (dd, 1H), 2.44 (dd, 1H), 2.81 (m, 1H), 3.12 (s, 3H), 4.18 (m, 1H), 4.36 (m, 1H), 4.86 (m, 1H), 5.18 (m, 1H), 6.00 (d, 1H), 6.22 (d, 1H).

Preparation 36: Compound 38

Method: General Procedure 8.

Starting material: Compound 28.

Eluant (chromatography): 0% to 2% ether in pet.ether.

NMR: δ=0.06 (m, 12H), 0.09 (s, 9H), 0.62 (s, 3H), 0.87 (s, 9H), 0.88 (s, 9H), 1.15 (s, 3H), 1.19 (s, 6H), 1.10–2.05 (m, 21H), 2.21 (dd, 1H), 2.43 (dd, 1H), 2.81 (m, 1H), 3.12 (s, 3H), 4.18 (m, 1H), 4.37 (m, 1H), 4.86 (m, 1H), 5.18 (m, 1H), 6.00 (d, 1H), 6.22 (d, 1H).

Preparation 37: Compound 39

Method: General Procedure 8.

Starting material: Compound 29.

Eluant (chromatography): 0% to 2% ether in pet.ether.

NMR: δ=0.05 (m, 12H), 0.09 (s, 9H), 0.63 (s, 3H), 0.81 (s, 6H), 0.86 (s, 9H), 0.87 (s, 9H), 1.10 (t, 3H), 1.17 (s, 3H), 1.46 (q, 4H), 1.00–2.05 (m, 19H), 2.21 (dd, 1H), 2.44 (dd, 1H), 2.81 (m, 1H), 3.32 (m, 2H), 4.18 (m, 1H), 4.37 (m, 1H), 4.86 (m, 1H), 5.18 (m, 1H), 6.01 (d, 1H), 6.22 ( d, 1H).

Preparation 38: Compound 40

Method: General Procedure 9.

Starting material: Compound 18.

Eluant (chromatography): 0% to 10% ether in pet.ether.

NMR: δ=0.06 (m, 12H), 0.73 (m, 3H), 0.81 (t, 6H), 0.86 (s, 9H), 0.87 (s, 9H), 1.32 (s, 3H), 1.15–2.37 (m, 28H), 2.43 (dd, 1H) 2.79 (bd 1H), 3.30 (s, 3H) 3.42 (m 1H), 3.93 (m, 1H), 4.18 (m, 1H), 4.37 (m, 1H), 4.65 (m, 1H), 4.86 (m, 1H), 5.18 (m, 1H), 5.99 (d, 1H), 6.22 (d, 1H).

Preparation 39: Compound 41

Method: General Procedure 11.

Starting material: Compound 16.

Eluant (chromatography): 50% to 0% ether in ethyl acetate.

NMR: δ=0.82 (s, 3H), 0.87 (t, 3H), 0.88 (t, 3H), 1.46 (s, 3H), 1.25–2.10 (m, 25H), 2.16 (bd, 1H), 2.32 (dd, 1H), 2.45 (s, 2H), 2.60 (dd, 1H), 2.82 (m, 1H), 3.46 (m, 1H), 3.96 (m, 1H), 4.22 (m, 1H), 4.44 (m, 1H), 4.82 (m, 1H), 5.00 (m, 1H), 5.34 (m, 1H), 6.01 (d, 1H), 6.38 (d, 1H).

Preparation 40: Compound 42

Method: General Procedure 11.

Starting material: Compound 17.

Eluant (chromatography): 50% to 0% ether in ethyl acetate.

NMR: δ=0.73 (s, 3H), 0.87 (t, 3H), 0.88 (t, 3H), 1.48 (s, 3H), 1.20–2.10 (m, 25H), 2.18 (bd, 1H), 2.32 (dd, 1H), 2.46 (s, 2H), 2.60 (dd, 1H), 2.83 (m, 1H), 3.46 (m, 1H), 3.97 (m, 1H), 4.24 (m, 1H), 4.44 (m, 1H), 4.81 (m, 1H), 5.00 (m, 1H), 5.33 (m, 1H), 6.02 (d, 1H), 6.38 (d, 1H).

Preparation 41: Compound 43

Method: General Procedure 11.

Starting material: Compound 18.

Eluant (chromatography): 50% to 0% pet.ether in ethyl acetate.

NMR: δ=0.81 (s, 3H), 0.82 (t, 6H), 1.45 (s, 3H), 1.20–2.40 (m, 31H), 2.60 (dd, 1H), 2.83 (m, 1H), 3.45 (m, 1H), 3.94 (m, 1H), 4.23 (m, 1H), 4.43 (m, 1H), 4.67 (m, 1H), 5.00 (m, 1H), 5.33 (m, 1H), 6.02 (d, 1H), 6.37 (d, 1H).

Preparation 42: Compound 44

Method: General Procedure 11.

Starting material: Compound 19.

Eluant (chromatography): 50% to 0% pet.ether in ethyl acetate.

NMR: δ=0.82 (s, 3H), 0.83 (t, 6H), 1.46 (s, 3H), 1.20–2.25 (m, 32H), 2.32 (dd, 1H), 2.60 (dd, 1H), 2.83 (m, 1H), 3.45 (m, 1H), 3.95 (m, 1H), 4.23 (m, 1H), 4.44 (m, 1H), 4.72 (m, 1H), 5.00 (m, 1H), 5.33 (m, 1H), 6.02 (d, 1H), 6.38 (d, 1H).

Preparation 43: Compound 45

Method: General Procedure 11.

Starting material: Compound 35.

Eluant (chromatography): 50% to 0% pet.ether in ethyl acetate.

NMR: δ=0.77 (s, 3H), 0.88 (t, 3H), 0.89 (t, 3H), 1.16 (t, 3H), 1.35 (s, 3H), 1.20–2.15 (m, 24H), 2.22 (bd, 1H), 2.32 (dd, 1H), 2.47 (s, 2H), 2.60 (dd, 1H), 2.81 (m, 1H), 3.45 (m, 1H), 3.50 (m, 1H), 3.70 (m, 1H), 3.97 (m, 1H), 4.23 (m, 1H), 4.43 (m, 1H), 4.81 (m, 1H), 5.01 (m, 1H), 5.33 (m, 1H), 6.00 (d, 1H), 6.38 (d, 1H).

Preparation 44: Compound 46

Method: General Procedure 11.

Starting material: Compound 36.

Eluant (chromatography): 50% to 0% pet.ether in ethyl acetate.

NMR: δ=0.75 (s, 3H), 0.88 (t, 3H), 0.89 (t, 3H), 1.35 (s, 3H), 1.20–2.10 (m, 24H), 2.18 (bd, 1H), 2.31 (dd, 1H), 2.49 (m, 2H), 2.60 (dd, 1H), 2.81 (m, 1H), 3.32 (s, 1H), 3.45 (m, 1H), 3.97 (m, 1H), 4.23 (m, 1H), 4.43 (m, 1H), 4.82 (m, 1H), 5.00 (m, 1H), 5.33 (m, 1H), 6.00 (d, 1H), 6.37 (d, 1H).

Preparation 45: Compound 47

Method: General Procedure 11.

Starting material: Compound 40.

Eluant (chromatography): 50% to 0% pet.ether in ethyl acetate.

NMR: δ=0.75 (s, 3H), 0.83 (t, 6H), 1.33 (s, 3H), 1.20–2.40 (m, 30H), 2.60 (dd, 1H), 2.81 (m, 1H), 3.31 (s, 3H), 3.45 (m, 1H), 3.94 (m, 1H), 4.23 (m, 1H), 4.43 (m, 1H), 4.68 (m, 1H), 5.00 (m, 1H), 5.33 (m, 1H), 6.00 (d, 1H), 6.38 (d, 1H).

Preparation 46: Compound 48

Method: General Procedure 10.

Starting material: 1-bromo-4-(1-propyl)-4-trimethyl-silyloxy-heptane.

Eluant (chromatography): 2% ether in pet.ether.

NMR: δ=0.05 (m, 12H), 0.09 (s, 9H), 0.71 (s, 3H), 0.85 (s, 9H), 0.88 (t, 6H), 0.89 (s, 9H), 1.28 (s, 3H), 1.10–2.20 (m, 28H), 2.29 (bd, 1H), 2.56 (dd, 1H), 2.87 (m, 1H), 4.21 (m, 1H), 4.53 (m, 1H), 4.94 (m, 1H), 4.98 (m, 1H), 5.82 (d, 1H), 6.45 (m, 1H).

Preparation 47: Compound 49

Method: General Procedure 10.

Starting material: 1-bromo-4-methyl-4-trimethylsilyloxy-pentane.

Eluant (chromatography): 5% ether in pet.ether.

NMR: δ=0.06 (m, 12H), 0.10 (s, 9H), 0.71 (s, 3H), 0.85 (s, 9H), 0.89 (s, 9H), 1.21 (s, 6H), 1.28 (s, 3H), 1.10–2.15 (m, 20H), 2.29 (bd, 1H), 2.56 (dd, 1H), 2.87 (m, 1H), 4.21 (m, 1H), 4.53 (m, 1H), 4.94 (m, 1H), 4.98 (m, 1H), 5.82 (m, 1H), 6.45 (m, 1H).

Preparation 48: Compound 50

Method: General Procedure 9.

Starting material: Compound 58 and methyl iodide.

Eluant (chromatography): 1% ether in pet.ether.

NMR: δ=0.05 (m, 12H), 0.08 (s, 9H), 0.63 (s, 3H), 0.86 (s, 9H), 0.89 (s, 9H), 0.80–0.95 (m, 6H), 1.17 (s, 3H), 1.10–2.10 (m, 27H), 2.30 (bd, 1H), 2.55 (dd, 1H), 2.86 (m, 1H), 3.12 (s, 3H), 4.21 (m, 1H), 4.53 (m, 1H), 4.93 (m, 1H), 4.98 (m, 1H), 5.81 (d, 1H), 6.45 (d, 1H).

Preparation 49: Compound 51

Method: General Procedure 9.

Starting material: Compound 49 and methyl iodide.

Eluant (chromatography): 3% ether in pet.ether.

NMR: δ=0.05 (m, 12H), 0.10 (s, 9H), 0.63 (s, 3H), 0.86 (s, 9H), 0.89 (s, 9H), 1.17 (s, 3H), 1.21 (s, 6H), 1.10–2.10 (m, 19H), 2.30 (bd, 1H), 2.55 (dd, 1H), 2.86 (bd, 1H), 3.13 (s, 3H), 4.21 (m, 1H), 4.53 (m, 1H), 4.93 (m, 1H), 4.98 (m, 1H), 5.81 (d, 1H), 6.45 (d, 1H).

Preparation 50: Compound 52

Method: General Procedure 9.

Starting material: Compound 22 and methyl iodide.

Eluant (chromatography): 2% ether in pet.ether.

NMR: δ=0.05 (m, 12H), 0.09 (s, 9H), 0.63 (s, 3H), 0.80 (t, 6H), 0.85 (s, 9H), 0.89 (s, 9H), 1.16 (s, 3H), 1.44 (q, 4H), 1.10–2.10 (m, 21H), 2.30 (bd, 1H), 2.55 (dd, 1H), 2.86 (bd, 1H), 3.13 (s, 3H), 4.21 (m, 1H), 4.53 (m, 1H), 4.93 (m, 1H), 4.98 (m, 1H), 5.81 (d, 1H), 6.45 (d, 1H).

Preparation 51: Compound 53

Method: General Procedure 9.

Starting material: Compound 22 and ethyl iodide.

Eluant (chromatography): 1% ether in pet.ether.

NMR: δ=0.06 (m, 12H), 0.10 (s, 9H), 0.64 (s, 3H), 0.80 (t, 6H), 0.87 (s, 9H), 0.89 (s, 9H), 1.10 (t, 3H), 1.17 (s, 3H), 1.44 (q, 4H), 1.05–2.05 (m, 21H), 2.32 (bd, 1H), 2.54 (dd, 1H), 2.86 (bd, 1H), 3.33 (s, 2H), 4.21 (m, 1H), 4.52 (m, 1H), 4.93 (m, 1H), 4.98 (m, 1H), 5.81 (d, 1H), 6.45 (d, 1H).

Preparation 52: Compound 54

Method: General Procedure 8.

Starting material: Compound 61.

Eluant (chromatography): 30% ethyl acetate in pet.ether.

NMR: δ=0.05 (m, 12H), 0.60–0.72 (s, 3H), 0.77–0.95 (m, 24H), 1.46 (q, 4H), 1.52–1.57 (s, 3H), 1.00–2.10 (m, 20H), 2.20 (dd, 1H), 2.42 (dd, 1H), 2.50–2.60 (s, 3H), 2.80 (m, 1H), 4.18 (m, 1H), 4.37 (m, 1H), 4.85 (m, 1H), 5.19 (m, 1H), 6.00 (d, 1H), 6.20 (d, 1H).

Preparation 53: Compound 55

Method: General Procedure 8.

Starting material: Compound 48.

Eluant (chromatography): 2% ethyl acetate in pet.ether.

NMR: δ=0.05 (m, 12H), 0.08 (s, 9H), 0.70 (s, 3H), 0.86 (s, 18H), 0.87 (t, 6H), 1.27 (s, 3H), 1.10–2.15 (m, 28H), 2.21 (dd, 1H), 2.44 (dd, 1H), 2.82 (m, 1H), 4.17 (m, 1H), 4.37 (m, 1H), 4.85 (m, 1H), 5.17 (m, 1H), 6.01 (d, 1H), 6.22 (d, 1H).

Preparation 54: Compound 56

Method: General Procedure 8.

Starting material: Compound 50.

Eluant (chromatography): 1% ether in pet.ether.

NMR: δ=0.06 (m, 12H), 0.08 (s, 9H), 0.62 (s, 3H), 0.86 (s, 9H), 0.87 (s, 9H), 0.75–1.0 (m, 6H), 1.16 (s 3H), 1.10–2.05 (m, 27H), 2.21 (dd, 1H), 2.43 (dd, 1H), 2.81 (m, 1H), 3.12 (s, 3H), 4.18 (m, 1H), 4.37 (m, 1H), 4.86 (m, 1H), 5.18 (m, 1H), 6.00 (d, 1H), 6.22 (d, 1H).

Preparation 55: Compound 57

Method: General Procedure 8.

Starting material: Compound 49.

Eluant (chromatography): 20% ethyl acetate in pet.ether.

NMR: δ=0.05 (m, 12H), 0.10 (s, 9H), 0.70 (s, 3H), 0.86 (s, 18H), 1.20 (s, 6H), 1.27 (s, 3H), 1.10–2.15 (m, 20H), 2.20 (d, 1H), 2.44 (dd, 1H), 2.81 (m, 1H), 4.18 (m, 1H), 4.36 (m, 1H), 4.86 (m, 1H), 5.17 (m, 1H), 6.00 (d, 1H), 6.22 (d, 1H).

Preparation 56: Compound 58

Method: General Procedure 8.

Starting material: Compound 51.

Eluant (chromatography): 3% ethyl acetate in pet.ether.

NMR: δ=0.06 (m, 12H), 0.09 (s, 9H), 0.62 (s, 3H), 0.86 (s, 9H), 0.87 (s, 9H), 1.16 (s, 3H), 1.20 (s, 6H), 1.10–2.05 (m, 19H), 2.20 (dd, 1H), 2.43 (dd, 1H), 2.81 (m, 1H), 3.12 (s, 3H); 4.18 (m, 1H), 4.36 (m, 1H), 4.86 (m, 1H), 5.18 (m, 1H), 6.00 (d, 1H), 6.22 (d, 1H).

Preparation 57: Compound 59

Method: General Procedure 8.

Starting material: Compound 52.

Eluant (chromatography): 1% ether in pet.ether.

NMR: δ=0.06 (m, 12H), 0.09 (s, 9H), 0.62 (s, 3H), 0.80 (t, 6H), 0.86 (s, 9H), 0.87 (s, 9H), 1.15 (s, 3H), 1.44 (q, 4H), 1.10–2.05 (m, 21H), 2.21 (dd, 1H), 2.43 (dd, 1H), 2.81 (m, 1H), 3.12 (s, 3H), 4.18 (m, 1H), 4.37 (m, 1H), 4.86 (m, 1H), 5.18 (m, 1H), 6.00 (d, 1H), 6.22 (dd, 1H).

Preparation 58: Compound 60

Method: General Procedure 8.

Starting material: Compound 53.

Eluant (chromatography): 1% ether in pet.ether.

NMR: δ=0.05 (m, 12H), 0.09 (s, 9H), 0.63 (s, 3H), 0.80 (t, 6H), 0.86 (s, 9H), 0.88 (s, 9H), 1.10 (t, 3H), 1.16 (s, 3H), 1.44 (q, 4H), 1.05–2.05 (m, 21H), 2.21 (dd, 1H), 2.43 (dd, 1H), 2.81 (m, 1H), 3.32 (m, 2H), 4.18 (m, 1H), 4.37 (m, 1H), 4.86 (m, 1H), 5.19 (m, 1H), 6.00 (d, 1H), 6.22 (d, 1H).

Preparation 59: Compound 61

Method: General Procedure 14.

Starting material: Compound 21 and methanesulfinyl chloride.

Eluant (chromatography): 20% ether in pet.ether.

NMR: δ=0.05 (m, 12H), 0.09 (s, 9H), 0.60–0.73 (s, 3H), 0.75–1.00 (m, 24H), 1.50–1.60 (s, 3H), 1.10–2.10 (m, 23H), 2.31 (m, 1H), 2.45–2.60 (m, 4H), 2.86 (m, 1H), 4.21 (m, 1H), 4.52 (m, 1H), 4.93 (m, 1H), 4.98 (m, 1H), 5.81 (d, 1H), 6.43 (d, 1H).

Preparation 60: Compound 62

Method: General Procedure 10.

Starting material: 1-bromo-4-methyl-pentane.

Eluant (chromatography): 5% ether in pet.ether.

NMR: δ=0.05 (m, 12H), 0.71 (s, 3H), 0.85 (s, 9H), 0.89 (s, 9H), 0.82–0.92 (m, 6H), 1.27 (s, 3H), 1.05–2.20 (m, 21H), 2.30 (bd, 1H), 2.56 (dd, 1H), 2.86 (bd, 1H), 4.21 (m, 1H), 4.53 (m, 1H), 4.94 (m, 1H), 4.98 (m, 1H), 5.81 (d, 1H), 6.45 (d, 1H).

Preparation 61: Compound 63

Method: General Procedure 8.

Starting material: Compound 62.

Eluant (chromatography): 5% ether in pet.ether.

NMR: δ=0.05 (m, 12H), 0.70 (s, 3H), 0.87 (s, 18H), 0.82–0.90 (m, 6H), 1.26 (s, 3H), 1.05–2.15 (m, 21H), 2.20 (dd, 1H), 2.43 (dd, 1H), 2.80 (m, 1H), 4.18 (m, 1H), 4.36 (m, 1H), 4.86 (m, 1H), 5.17 (m, 1H), 6.00 (d, 1H), 6.22 (d, 1H).

Preparation 62: Compound 64

Method: General Procedure 9.

Starting material: Compound 62 and methyl iodide.

Eluant (chromatography): 2% ether in pet.ether.

NMR: δ=0.05 (m, 12H), 0.62 (s, 3H), 0.85 (s, 9H), 0.90 (s, 9H), 0.70–0.95 (m, 6H), 1.16 (s, 3H), 1.05–2.10 (m, 20H), 2.30 (bd, 1H), 2.55 (dd, 1H), 2.86 (m, 1H), 3.12 (s, 3H), 4.21 (m, 1H), 4.53 (m, 1H), 4.93 (m, 1H), 4.98 (m,1H), 5.81 (d, 1H), 6.45 (d, 1H).

Preparation 63: Compound 65

Method: General Procedure 8.

Starting material: Compound 64.

Eluant (chromatography): 1% ether in pet.ether.

NMR: δ=0.06 (m, 12H), 0.62 (s, 3H), 0.87 (s, 9H), 0.88 (s, 9H), 0.80–1.05 (m, 6H), 1.15 (s, 3H), 1.05–2.05 (m, 20H), 2.21 (dd, 1H), 2.44 (dd, 1H), 2.81 (m, 1H), 3.12 (s, 3H), 4.18 (m, 1H), 4.37 (m, 1H), 4.86 (m, 1H), 5.18 (m, 1H), 6.00 (d, 1H), 6.23 (d, 1H).

EXAMPLE 1:
1(S),3(R),20(R)-Trihydroxy-20-(4-ethyl-4-hydroxy-1-hexyn-1-yl)-9,10-secopregna-5(Z),7(E),10(19)-triene (Compound 101)

Method: General Procedure 12.

Starting material: Compound 41.

Eluant (chromatography): 50% to 0% pet.ether in ethyl acetate.

NMR: $\delta$=0.82 (s, 3H), 0.88 (t, 6H), 1.48 (s, 3H), 1.25–2.10 (m, 20H), 2.17 (bd, 1H), 2.31 (dd, 1H), 2.36 (s, 2H), 2.60 (dd, 1H), 2.82 (m, 1H), 4.23 (m, 1H), 4.43 (m, 1H), 5.00 (m, 1H), 5.33 (m, 1H), 6.01 (d, 1H), 6.37 (d, 1H).

EXAMPLE 2:
1(S),3(R),20(S)-Trihydroxy-20-(4-ethyl-4-hydroxy-1-hexyn-1-yl)-9,10-secopregna-5(Z),7(E),10(19)-triene (Compound 102)

Method: General Procedure 12.

Starting material: Compound 42.

Eluant (chromatography): 50% to 0% pet.ether in ethyl acetate.

NMR: $\delta$=0.73 (s, 3H), 0.89 (t, 6H), 1.51 (s, 3H), 1.20–2.10 (m, 20H), 2.18 (bd, 1H), 2.32 (dd, 1H), 2.37 (s, 2H), 2.60 (dd, 1H), 2.83 (m, 1H), 4.24 (m, 1H), 4.44 (m, 1H), 5.00 (m, 1H), 5.33 (m, 1H), 6.02 (d, 1H), 6.37 (d, 1H).

EXAMPLE 3:
1(S),3(R)-Dihydroxy-20(R)-methoxy-20-(4-ethyl-4-hydroxy-1-hexyn-1-yl)-9,10-secopregna-5(Z),7(E),-10(19)-triene (Compound 103)

Method: General Procedure 12.

Starting material: Compound 46.

Eluant (chromatography): 50% to 0% pet.ether in ethyl acetate.

NMR: $\delta$=0.76 (s, 3H), 0.89 (t, 6H), 1.37 (s, 3H), 1.20–2.10 (m, 19H), 2.18 (bd, 1H), 2.31 (dd, 1H), 2.39 (s, 2H), 2.59 (dd, 1H), 2.81 (m, 1H), 3.32 (s, 3H), 4.22 (m, 1H), 4.43 (m, 1H), 5.00 (m, 1H), 5.33 (m, 1H), 6.00 (d, 1H), 6.37 (d, 1H).

EXAMPLE 4:
1(S),3(R)-Dihydroxy-20(R)-ethoxy-20-(4-ethyl-4-hydroxy-1-hexyn-1-yl)-9,10-secopregna -5(Z),7(E),-10(19)-triene (Compound 104)

Method: General Procedure 12.

Starting material: Compound 45.

Eluant (chromatography): 50% to 0% pet.ether in ethyl acetate.

NMR: $\delta$=0.77 (s, 3H), 0.89 (t, 6H), 1.26 (t, 3H), 1.37 (s, 3H), 1.20–2.10 (m, 19H), 2.22 (bd, 1H), 2.31 (dd, 1H), 2.38 (s, 2H), 2.60 (dd, 1H), 2.81 (m, 1H), 3.51 (m, 3H), 3.68 (m, 1H), 4.23 (m, 1H), 4.43 (m, 1H), 5.01 (m, 1H), 5.33 (m, 1H), 6.00 (d, 1H), 6.38 (d, 1H).

EXAMPLE 5:
1(S),3(R),20(R)-Trihydroxy-20-(5-ethyl-5-hydroxy-1-heptyn-1-yl)-9,10-secopregna-5(Z),7(E),10(19)-triene (Compound 105)

Method: General Procedure 12.

Starting material: Compound 43.

Eluant (chromatography): 50% to 0% pet.ether in ethyl acetate.

NMR: $\delta$=0.81 (s, 3H), 0.86 (t, 6H), 1.45 (s, 3H), 1.20–2.10 (m, 22H), 2.16 (bd, 1H), 2.25 (t, 2H), 2.32 (dd, 1H), 2.59 (dd, 1H), 2.83 (m, 1H), 4.23 (m, 1H), 4.42 (m, 1H), 5.01 (m, 1H), 5.33 (m, 1H), 6.02 (d, 1H), 6.37 (d, 1H).

EXAMPLE 6:
1((S),3(R)-Dihydroxy-20(R)-methoxy-20-(5-ethyl-5-hydroxy-1-heptyn-1-yl)-9,10-secopregna-5(Z),7(E),-10(19)-triene (Compound 106)

Method: General Procedure 12.

Starting material: Compound 47.

Eluant (chromatography): 50% to 0% pet.ether in ethyl acetate.

NMR: $\delta$=0.75 (s, 3H), 0.87 (t, 6H), 1.34 (s, 3H), 1.48 (q, 4H), 1.67 (t, 2H), 1.20–2.10 (m, 15H), 2.17 (bd, 1H), 2.28 (t, 2H), 2.31 (dd, 1H), 2.60 (dd, 1H), 2.81 (m, 1H), 3.31 (s, 3H), 4.23 (m, 1H), 4.43 (m, 1H), 5.01 (m, 1H), 5.33 (m, 1H), 6.00 (d, 1H), 6.38 (d, 1H).

EXAMPLE 7:
1(S),3(R),20(R)-Trihydroxy-20-(6-ethyl-6-hydroxy-1-octyn-1-yl)-9,10-secopregna-5(Z),7(E),10(19)-triene (Compound 107)

Method: General Procedure 12.

Starting material: Compound 44.

Eluant (chromatography): 50% to 0% pet.ether in ethyl acetate.

NMR: $\delta$=0.82 (s, 3H), 0.87 (t, 6H), 0.88 (t, 3H), 1.46 (s, 3H), 1.20–2.25 (m, 27H), 2.31 (dd, 1H), 2.60 (dd, 1H), 2.83 (m, 1H), 4.23 (m, 1H), 4.43 (m, 1H), 5.00 (m, 1H), 5.33 (m, 1H), 6.02 (d, 1H), 6.38 (d, 1H).

EXAMPLE 8:
1(S),3(R),20(S)-Trihydroxy-20-(3-methyl-3-hydroxy-1-butyl)-9,10-secopregna-5(Z),7(E),10(19)-triene (Compound 108)

Method: General Procedure 11.

Starting material: Compound 30.

Eluant (chromatography): 20% pet.ether in ethyl acetate.

NMR: $\delta$=0.73 (s, 3H), 1.21 (s, 3H), 1.23 (s, 3H), 1.28 (s, 3H), 1.05–2.20 (m, 21H), 2.32 (dd, 1H), 2.60 (dd, 1H), 2.82 (m, 1H), 4.23 (m, 1H), 4.43 (m, 1H), 5.00 (m, 1H), 5.33 (m, 1H), 6.02 (d, 1H), 6.37 (d, 1H).

EXAMPLE 9:
1(S),3(R),20(S)-Trihydroxy-20-(4-ethyl-4-hydroxy-1-hexyl)-9,10-secopregna-5(Z),7(E),10(19)-triene (Compound 109)

Method: General Procedure 11.

Starting material: Compound 31.

Eluant (chromatography): 20% pet.ether in ethyl acetate.

NMR: $\delta$=0.72 (s, 3H), 0.86 (t, 6H), 1.28 (s, 3H), 1.48 (q, 4H), 1.15–2.15 (m, 23H), 2.32 (dd, 1H), 2.59 (dd, 1H), 2.83 (m, 1H), 4.23 (m, 1H), 4.43 (m, 1H), 5.00 (m, 1H), 5.33 (m, 1H), 6.02 (d, 1H), 6.37 (d, 1H).

EXAMPLE 10: 1(S),3(R)-Dihydroxy-20(S)-methoxy-20-(4-ethyl-4-hydroxy-1-hexyl)-9,10-secopregna -5(Z),7(E),10(19)-triene (Compound 110)

Method: General Procedure 11.

Starting material: Compound 37.

Eluant (chromatography): 50% to 0% pet.ether in ethyl acetate.

NMR: δ=0.64 (s, 3H), 0.86 (t, 6H), 1.17 (s, 3H), 1.48 (q, 4H), 1.15–2.10 (m, 22H), 2.31 (dd, 1H), 2.59 (dd, 1H), 2.82 (m, 1H), 3.13 (s, 3H), 4.23 (m, 1H), 4.43 (m, 1H), 5.00 (m, 1H), 5.33 (m, 1H), 6.02 (d, 1H), 6.37 (d, 1H).

EXAMPLE 11: 1(S),3(R)-Dihydroxy-20(S)-ethoxy-20-(4-ethyl-4-hydroxy-1-hexyl)-9,10-secopregna-5(Z), 7(E),-10(19)-triene (Compound 111)

Method: General Procedure 11.

Starting material: Compound 39.

Eluant (chromatography): 50% to 20% pet.ether in ethyl acetate.

NMR: δ=0.65 (s, 3H), 0.86 (t, 6H), 1.10 (t, 3H), 1.18 (s, 3H), 1.47 (q, 4H), 1.00–2.10 (m, 22H), 2.31 (dd, 1H), 2.59 (dd, 1H), 2.82 (m, 1H), 2.33 (m, 2H), 4.23 (m, 1H), 4.43 (m, 1H), 5.00 (m, 1H), 5.33 (m, 1H), 6.01 (d, 1H), 6.37 (d, 1H).

EXAMPLE 12: 1(S),3(R),20(S)-Trihydroxy-20-(5-methyl-5-hydroxy-1-hexyl)-9,10-secopregna-5(Z),7(E), 10(19)-triene (Compound 112)

Method: General Procedure 11.

Starting material: Compound 34.

Eluant (chromatography): 20% pet.ether in ethyl acetate.

NMR: δ=0.73 (s, 3H), 1.21 (s, 6H), 1.27 (s, 3H), 1.10–2.15 (m, 25H), 2.32 (dd, 1H), 2.60 (dd, 1H), 2.83 (m, 1H), 4.23 (m, 1H), 4.43 (m, 1H), 5.00 (m, 1H), 5.33 (m, 1H), 6.02 (d, 1H), 6.37 (d, 1H).

EXAMPLE 13: 1(S),3(R)-Dihydroxy-20-(S)-methoxy-20-(5-methyl-5-hydroxy-1-hexyl)-9,10-secopregna-5(Z),7(E), 10(19)-triene (Compound 113)

Method: General Procedure 11.

Starting material: Compound 38.

Eluant (chromatography): 50% to 20% pet.ether in ethyl acetate.

NMR: δ=0.64 (s, 3H), 1.16 (s, 3H), 1.21 (s, 6H), 1.10–2.10 (m, 24H), 2.31 (dd, 1H), 2.59 (dd, 1H), 2.82 (m, 1H), 3.13 (s, 3H), 4.23 (m, 1H), 4.43 (m, 1H), 4.99 (m, 1H), 5.33 (m, 1H), 6.02 (d, 1H), 6.37 (d, 1H).

EXAMPLE 14: 1(S),3(R),20(S)-Trihydroxy-20-(5-ethyl-5-hydroxy-1-heptyl)-9,10-secopregna-5(Z),7(E), 10(19)-triene (Compound 114)

Method: General Procedure 11.

Starting material: Compound 32.

Eluant (chromatography): 20% pet.ether in ethyl acetate.

NMR: δ=0.72 (s, 3H), 0.86 (t, 6H), 1.27 (s, 3H), 1.46 (q, 4H), 1.15–2.15 (m, 25H), 2.32 (dd, 1H), 2.60 (dd, 1H), 2.83 (m, 1H), 4.23 (m, 1H), 4.43 (m, 1H), 5.00 (m, 1H), 5.33 (m, 1H), 6.02 (d, 1H), 6.37 (d, 1H).

EXAMPLE 15: 1(S),3(R),20(S)-Trihydroxy-20-(6-methyl-6-hydroxy-1-heptyl)-9,10-secopregna-5(Z),7(E), 10(19)-triene (Compound 115)

Method: General Procedure 13.

Starting material: Compound 33.

Eluant (chromatography): ethyl acetate.

NMR: δ=0.71 (s, 3H), 1.19 (s, 6H), 1.25 (s, 3H), 1.00–2.15 (m, 27H), 2.30 (dd, 1H), 2.58 (dd, 1H), 2.81 (m, 1H), 4.22 (m, 1H), 4.42 (m, 1H), 4.98 (m, 1H), 5.32 (m, 1H), 6.00 (d, 1H), 6.36 (d, 1H).

EXAMPLE 16: 1(S),3(R)-Dihydroxy-20(S)-methyl-sulfinyloxy-20-(4-ethyl-4-hydroxy-1-hexyl)-9,10-secopregna -5(Z),7(E),10(19)-triene (Compound 116)

Method: General Procedure 11.

Starting material: Compound 54.

Eluant (chromatography): 50% ethyl acetate in pet.ether.

NMR: δ=0.60–0.75 (s, 3H), 0.86 (m, 6H), 1.20–2.12 (m, 29H), 2.32 (dd, 1H), 2.56–2.57 (s, 3H), 2.58 (m, 1H), 2.83 (m, 1H), 4.23 (m, 1H), 4.43 (m, 1H), 4.99 (m, 1H), 5.34 (m, 1H), 6.02 (d, 1H), 6.36 (d, 1H).

EXAMPLE 17: 1(S),3(R),20(S)-Trihydroxy-20-(4-(1-propyl)-4-hydroxy-1-heptyl)-9,10-secopregna-5(Z), 7(E),10(19)-triene (Compound 117)

Method: General Procedure 11.

Starting material: Compound 55.

Eluant (chromatography): 30% pet.ether i ethyl acetate.

NMR: δ=0.72 (s, 3H), 0.92 (t, 6H), 1.28 (s, 3H), 1.10–2.15 (m, 31H), 2.31 (dd, 1H), 2.59 (dd, 1H), 2.82 (m, 1H), 4.23 (m, 1H), 4.43 (m, 1H), 5.01 (m, 1H), 5.33 (m, 1H), 6.02 (d, 1H), 6.37 (d, 1H).

EXAMPLE 18: 1(S),3(R)-Dihydroxy-20(S)-methoxy-20-(4-(1-propyl)-4-hydroxy-1-hept-yl) -9,10-secopregna-5(Z),7(E),-10(19)-triene (Compound 118)

Method: General Procedure 11.

Starting material: Compound 56.

Eluant (chromatography): 50% ethyl acetate in pet.ether.

NMR: δ=0.64 (s, 3H), 0.92 (t, 6H), 1.17 (s, 3H), 1.10–2.10 (m, 30H), 2.31 (m, 1H), 2.59 (m, 1H), 2.82 (m, 1H), 3.13 (s, 3H), 4.23 (m, 1H), 4.43 (m, 1H), 4.99 (m, 1H), 5.33 (m, 1H), 6.01 (d, 1H), 6.37 (d, 1H).

EXAMPLE 19: 1(S),3(R),20(S)-Trihydroxy-20-(4-methyl-4-hydroxy-1-pentyl)-9,10-secopregna-5(Z),7(E), 10(19)-triene (Compound 119)

Method: General Procedure 11.

Starting material: Compound 57.

Eluant (chromatography): 100% ethyl acetate.

NMR: δ=0.72 (s, 3H), 1.23 (s, 6H), 1.29 (s, 3H), 1.10–2.15 (m, 23H), 2.31 (dd, 1H), 2.59 (m, 1H), 2.83 (m, 1H), 4.23 (m, 1H), 4.43 (m, 1H), 5.00 (m, 1H), 5.33 (m, 1H), 6.02 (d, 1H), 6.37 (d, 1H).

EXAMPLE 20:
1(S),3(R)-Dihydroxy-20(S)-methoxy-20-(4-methyl-4-hydroxy-1-pentyl)-9,10-secopregna-5(Z),7(E),10(19)-triene (Compound 120)

Method: General Procedure 11.

Starting material: Compound 58.

Eluant (chromatography): 100% ethyl acetate.

NMR: δ=0.64 (s, 3H), 1.18 (s, 3H), 1.23 (s, 6H), 1.15–2.10 (m, 22H), 2.31 (dd, 1H), 2.58 (m, 1H), 2.87 (m, 1H), 3.13 (s, 3H), 4.22 (m, 1H), 4.43 (m, 1H), 4.99 (m, 1H), 5.33 (m, 1H), 6.02 (d, 1H), 6.36 (m, 1H).

EXAMPLE 21:
1(S),3(R)-Dihydroxy-20-(S)-methoxy-20-(5-ethyl-5-hydroxy-1-heptyl)-9,10-secopregna-5(Z),7(E),-10(19)-triene (Compound 121)

Method: General Procedure 11.

Starting material: Compound 59.

Eluant (chromatography): 40% pet.ether in ethyl acetate.

NMR: δ=0.64 (s, 6H), 0.86 (t, 6H), 1.16 (s, 3H), 1.46 (q, 4H), 1.0–2.10 (m, 24H), 2.32 (dd, 1H), 2.59 (dd, 1H), 2.82 (m, 1H), 3.13 (s, 3H), 4.23 (m, 1H), 4.43 (m, 1H), 5.00 (m, 1H), 5.33 (m, 1H), 6.01 (d, 1H), 6.37 (m, 1H).

EXAMPLE 22: 1(S),3(R)-Dihydroxy-20-ethoxy-20-(5-ethyl-5-hydroxy-1-heptyl)-9,10-secopregna-5(Z),7(E),10(19)-triene (Compound 122)

Method: General Procedure 11.

Starting material: Compound 60.

Eluant (chromatography): 40% ethyl acetate in pet.ether.

NMR: δ=0.65 (s, 3H), 0.86 (t, 6H), 1.10 (t, 3H), 1.17 (s, 3H), 1.46 (q, 4H), 1.05–2.37 (m, 25H), 2.59 (m, 1H), 2.82 (m, 1H), 3.32 (m, 2H), 4.22 (m, 1H), 4.42 (m, 1H), 5.00 (m, 1H), 5.33 (m, 1H), 6.02 (d, 1H), 6.37 (d, 1H).

EXAMPLE 23:
1(S),3(R)-20(S)-Trihydroxy-20-(4-methyl-1-pentyl)-9,10-secopregna-5(Z),7(E),10(19)-triene (Compound 123)

Method: General Procedure 11.

Starting material: Compound 63.

Eluant (chromatography): 20% pet.ether in ethyl acetate.

NMR: δ=0.72 (s, 3H), 0.88 (d, 6H), 1.27 (s, 3H), 1.05–2.15 (m, 23H), 2.31 (dd, 1H), 2.59 (dd, 1H), 2.82 (m, 1H), 4.23 (m, 1H), 4.43 (m, 1H), 5.00 (m, 1H), 5.33 (m, 1H), 6.02 (d, 1H), 6.37 (d, 1H).

EXAMPLE 24:
1(S),3(R),-Dihydroxy-20(S)-methoxy-20-(4-methyl-1-pentyl)-9,10-secopregna-5(Z), 7(E),10(19)-triene (Compound 124)

Method: General Procedure 11.

Starting material: Compound 65.

Eluant (chromatography): 50% ethyl acetate in pet.ether.

NMR: δ=0.64 (s, 3H), 0.88 (d, 6H), 1.16 (s, 3H), 1.05–2.10 (m, 22H), 2.32 (dd, 1H), 2.59 (dd, 1H), 2.82 (m, 1H), 3.12 (s, 3H), 4.23 (m, 1H), 4.43 (m, 1H), 5.00 (m, 1H), 5.32 (m, 1H), 6.02 (d, 1H), 6.37 (d, 1H).

EXAMPLE 25

Capsulates Containing Compound 111

Compound 111 was dissolved in arachis oil to a final concentration of 1 µg of Compound 111/ml oil. 10 Parts by weight of gelatine, 5 parts by weight glycerine, 0.08 parts by weight potassium sorbate, and 14 parts by weight distilled water were mixed together with heating and formed into soft gelatine capsules. These were then filled each with 100 µl of Compound 111 in oil solution, such that each capsule contained 0.1 µg of Compound 111.

EXAMPLE 26

Dermatological Cream Containing Compound 111

In 1 g almond oil was dissolved 0.05 mg of Compound 111. To this solution was added 40 g of mineral oil and 20 g of self-emulsifying beeswax. The mixture was heated to liquify. After the addition of 40 ml hot water, the mixture was mixed well. The resulting cream contains approximately 0.5 µg of Compound 111 per gram of cream.

What we claim is:

1. A compound of the formula I

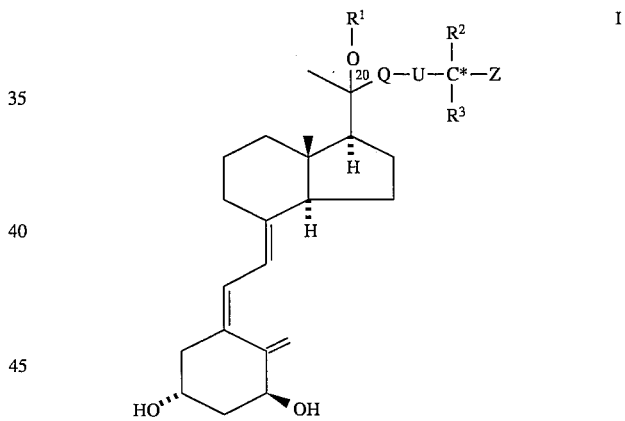

in which formula Q is a —$CH_2$—, —CH=CH— or —C≡C—; U is a $C_1$–$C_6$ alkylene; $R^1$ is hydrogen, a $C_1$–$C_4$ alkyl or YR' in which Y stands for the radicals —SO— or —$SO_2$— and R' stands for a $C_1$–$C_4$ alkyl; $R^2$ and $R^3$ are independently hydrogen or $C_1$–$C_4$ alkyl, and additionally $R^2$ and $R^3$, when taken together with the starred carbon atom, may form a $C_3$–$C_6$ carbocyclic ring; Z is hydrogen or hydroxy; and prodrugs of I in which one or more of the hydroxy groups are masked as groups which can be reconverted to hydroxy groups in vivo.

2. A compound of formula I of claim 1 in which Q is —$CH_2$—, U is —$(CH_2)_2$— or —$(CH_2)_3$—, $R^1$ is hydrogen, methyl or ethyl, $R^2$ and $R^3$ are methyl or ethyl and Z is hydroxy.

3. A diastereoisomer of a compound according to any one of claims 1–2.

4. A diastereoisomer of a compound according to claim 3 having a saturated side chain with the S-configuration at C-20.

5. A compound according to claim 1 which is a) 1(S),3(R),20(S)-Trihydroxy-20-(4-ethyl-4-hydroxy-1-hexyl)-9,10-secopregna-5(Z),7(E),10(19)-triene, b) 1(S),3(R)-Dihydroxy-20(S)-methoxy-20-(4-ethyl-4-hydroxy-1-hexyl)-9,10-secopregna-5(Z),7(E),10(19)-triene or c) 1(S),3(R)-Dihydroxy-20(S)-ethoxy-20-(4-ethyl-4-hydroxy-1-hexyl)-9,10-secopregna-5(Z),7(E),10(19)-triene.

6. A method for producing a compound of formula I of claim 1 in which a) an anion R⁻ is added to 1(S),1(R)-bis-(tert-butyldimethylsilyl-oxy)-9,10-secopregna-5(E), 7(E),10(19)-triene-20-one to form a compound of formula II

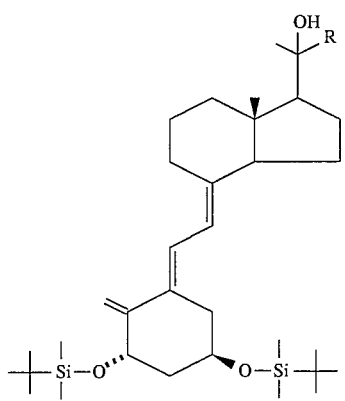

in which R is Q-U-C(R²)(R³)Z¹, Z² being hydrogen or OR⁴, where OR⁴ stands for hydroxy or for a protected hydroxy group, and Q, U, R² and R³ are as defined in claim 1; whereafter b) a compound of the above formula II is alkylated or acylated with R¹X¹ where X¹ is a leaving group to form a compound of formula III

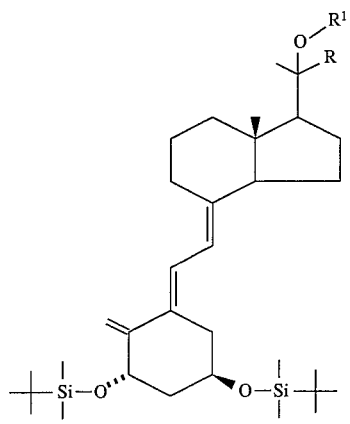

R¹ is as defined in claim 1, except for hydrogen; and then c) a compound of formula II or III is subjected to a triplet-sensitized photoisomerisation and deprotection, to form the desired compound of formula I.

7. A pharmaceutical composition containing an effective amount of at least one of the compounds of claim 1, together with a pharmaceutically acceptable, non-toxic carrier.

8. A pharmaceutical composition according to claim 7 in dosage unit form containing from 0.1 ppm to 0.1% by weight of the dosage unit of a compound of formula I.

9. A method for the treatment of a disease state selected from the group consisting of hyperparathyroidism, hypertension, acne, imbalance in the immune system, inflammatory diseases, diseases characterized by abnormal cell differentiation and/or cell proliferation, steroid induced skin atrophy, promotion of osteogenesis and treatment of osteoporosis, consisting of administering to a patient in need thereof an effective amount of a pharmaceutical composition according to claim 7.

\* \* \* \* \*